(12) United States Patent
Torabi et al.

(10) Patent No.: US 12,340,310 B2
(45) Date of Patent: Jun. 24, 2025

(54) ENERGY TOOL ACTIVATION DETECTION IN SURGICAL VIDEOS USING DEEP LEARNING

(71) Applicant: Verb Surgical Inc., Santa Clara, CA (US)

(72) Inventors: Meysam Torabi, Union City, CA (US); Varun Goel, Santa Clara, CA (US); Jocelyn Elaine Barker, San Jose, CA (US); Rami Abukhalil, Santa Clara, CA (US); Richard W. Timm, Cincinnati, OH (US); Pablo E. Garcia Kilroy, Menlo Park, CA (US)

(73) Assignee: Verb Surgical Inc., Santa Clara, CA (US)

( * ) Notice: Subject to any disclaimer, the term of this patent is extended or adjusted under 35 U.S.C. 154(b) by 376 days.

(21) Appl. No.: 17/875,122

(22) Filed: Jul. 27, 2022

(65) Prior Publication Data
US 2024/0037385 A1 Feb. 1, 2024

(51) Int. Cl.
*G06N 3/08* (2023.01)
*G06N 3/045* (2023.01)

(52) U.S. Cl.
CPC ............... *G06N 3/08* (2013.01); *G06N 3/045* (2023.01)

(58) Field of Classification Search
None
See application file for complete search history.

(56) References Cited

U.S. PATENT DOCUMENTS

| | | | |
|---|---|---|---|
| 2020/0303065 A1* | 9/2020 | Venkataraman | G06Q 10/08 |
| 2021/0012868 A1* | 1/2021 | Wolf | A61B 17/00 |
| 2021/0089785 A1* | 3/2021 | He | G06F 18/2411 |

FOREIGN PATENT DOCUMENTS

WO WO-2021125056 A1 * 6/2021 ......... A61B 1/00009

OTHER PUBLICATIONS

Wang et al., Deep learning based multi-label classification for surgical tool presence detection in laparoscopic videos (Year: 2017).*
Unpublished U.S. Appl. No. 17/566,116 filed Dec. 30, 2021.

* cited by examiner

*Primary Examiner* — Ian L Lemieux
*Assistant Examiner* — Promotto Tajrian Islam
(74) *Attorney, Agent, or Firm* — Aikin & Gallant, LLP

(57) ABSTRACT

Embodiments described herein include a process for detecting energy tool activations. The process can begin by receiving a surgical video of a surgical procedure involving energy tool activations. The process then applies a sequence of sampling windows to the surgical video to generate a sequence of windowed samples of the surgical video. Next, for each windowed sample in the sequence of windowed samples, the process applies a deep-learning model to a sequence of video frames within the windowed sample to generate an activation/non-activation inference and a confidence level associated with the activation/non-activation inference for the windowed sample. As a result, a sequence of activation/non-activation inferences and a sequence of associated confidence levels are generated. The process subsequently identifies a sequence of activation events in the surgical video based on the sequence of activation/non-activation inferences and the sequence of associated confidence levels.

17 Claims, 17 Drawing Sheets

Table 1

| # | Model name | Keyframe location | Padding type | Win length | Stride | Threshold | F1 SCORE | ACT DUR ACC | ACT NUM ACC | ACT ACC |
|---|---|---|---|---|---|---|---|---|---|---|
| 1 | F1 | Right | Valid | 1.9 Sec | 0.5 Sec | 0.4 | 82.27 | 90.44 | 86.58 | 88.47 |
| 2 | F2 | Right | Valid | 1.9 Sec | 0.5 Sec | 0.5 | 81.92 | 90.18 | 86.24 | 88.17 |
| 3 | K1 | Right | Valid | 1.6 Sec | 0.5 Sec | 0.4 | 86.1 | 89.96 | 84.16 | 86.96 |
| 4 | K2 | Right | Valid | 1.6 Sec | 0.5 Sec | 0.5 | 85.9 | 90.62 | 85.17 | 87.81 |
| 5 | G1 | Right | Valid | 1.4 Sec | 0.5 Sec | 0.4 | 85.06 | 86.45 | 80.72 | 83.49 |
| 6 | G2 | Right | Valid | 1.4 Sec | 0.5 Sec | 0.5 | 85.32 | 88.8 | 81.89 | 85.21 |
| 7 | I1 | Right | Clamp | 1.4 Sec | 0.5 Sec | 0.4 | 75.57 | 83.47 | 80.19 | 81.8 |
| 8 | I2 | Right | Clamp | 1.4 Sec | 0.5 Sec | 0.5 | 76.32 | 89.58 | 83.71 | 86.55 |
| 9 | J1 | Center | Clamp | 1.4 Sec | 0.5 Sec | 0.4 | 86.64 | 87.08 | 80.44 | 83.63 |
| 10 | J2 | Center | Clamp | 1.4 Sec | 0.5 Sec | 0.5 | 86.63 | 89.3 | 81.2 | 85.06 |
| 11 | L1 | Center | Clamp | 1.6 Sec | 0.5 Sec | 0.4 | 86.09 | 85.8 | 83.51 | 84.64 |
| 12 | L2 | Center | Clamp | 1.6 Sec | 0.5 Sec | 0.5 | 86.77 | 89.04 | 84.72 | 86.83 |

FIG. 16

ENERGY DOSAGE TABLE (Table 2)

| | Case No. | Media Num | Source | Batch / Purpose | Procedure Type | AE Device | Total Presence Dur (sec) | Total Activation Dur (sec) | Number of Activations |
|---|---|---|---|---|---|---|---|---|---|
| 1 | | | | | | | C7 | C8 | C9 |
| 2 | 271 | 281 | RTAB | Baptist | Sleeve Gastrectomy | Harmonic Ace +7 | 782.8 | 452.2 | 44 |
| 3 | 273 | 283 | RTAB | Baptist | Sleeve Gastrectomy | Harmonic Ace +7 | 333.7 | 87.4 | 30 |
| 4 | 274 | 284 | RTAB | Baptist | Sleeve Gastrectomy | Harmonic Ace +7 | 279.3 | 89.3 | 35 |
| 5 | 277 | 287 | RTAB | Baptist | Sleeve Gastrectomy | Harmonic HD 1000i | 511.1 | 150.1 | 49 |
| 6 | 279 | 289 | RTAB | Baptist | Sleeve Gastrectomy | Harmonic HD 1000i | 516.8 | 176.7 | 43 |
| 7 | 280 | 290 | RTAB | Baptist | Sleeve Gastrectomy | Harmonic HD 1000i | 796.1 | 279.3 | 80 |
| 8 | 281 | 291 | RTAB | Baptist | Sleeve Gastrectomy | Harmonic HD 1000i | 727.7 | 209 | 46 |
| 9 | 282 | 292 | RTAB | Baptist | Sleeve Gastrectomy | Harmonic Ace +7 | 476.9 | 114 | 35 |
| 10 | 283 | 293 | RTAB | Baptist | Sleeve Gastrectomy | Harmonic Ace +7 | 288.8 | 76 | 27 |
| 11 | 284 | 294 | RTAB | Baptist | Sleeve Gastrectomy | Harmonic Ace +7 | 262.2 | 76 | 28 |
| 12 | 286 | 296 | RTAB | Baptist | Sleeve Gastrectomy | Harmonic Ace +7 | 243.2 | 98.8 | 33 |
| 13 | 287 | 297 | RTAB | Baptist | Sleeve Gastrectomy | Harmonic Ace +7 | 288.8 | 85.5 | 36 |
| 14 | 288 | 298 | RTAB | Baptist | Sleeve Gastrectomy | Harmonic Ace +7 | 155.8 | 68.4 | 26 |
| 15 | 289 | 299 | RTAB | Baptist | Sleeve Gastrectomy | Harmonic Ace +7 | 248.9 | 76 | 30 |
| 16 | 290 | 300 | RTAB | Baptist | Sleeve Gastrectomy | Harmonic Ace +7 | 229.9 | 66.5 | 31 |
| 17 | 291 | 301 | RTAB | Baptist | Sleeve Gastrectomy | Harmonic Ace +7 | 288.8 | 104.5 | 33 |
| 18 | 292 | 302 | RTAB | Baptist | Sleeve Gastrectomy | Harmonic Ace +7 | 220.4 | 68.4 | 29 |
| 19 | 293 | 303 | RTAB | Baptist | Sleeve Gastrectomy | Harmonic Ace +7 | 562.4 | 172.9 | 56 |
| 20 | 294 | 304 | RTAB | Baptist | Sleeve Gastrectomy | Harmonic Ace +7 | 172.9 | 53.2 | 22 |

FIG. 17

ENERGY TOOL ACTIVATION DETECTION IN SURGICAL VIDEOS USING DEEP LEARNING

TECHNICAL FIELD

The disclosed embodiments generally relate to providing machine-learning/deep-learning solutions to assist and improve surgeries. More specifically, the disclosed embodiments relate to building deep-learning-based energy tool activation detection models for predicting energy tool activation durations and activation count based on surgical videos.

BACKGROUND

Surgical videos contain highly valuable and rich information for real-time or off-line event detections, and off-line training, assessing and analyzing the quality of the surgeries and skills of the surgeons, and for improving the outcomes of the surgeries and skills of the surgeons. There are many surgical procedures which involve displaying and capturing video images of the surgical procedures. For example, almost all minimally invasive procedures (MIS), such as endoscopy, laparoscopy, and arthroscopy, involve using video cameras and video images to assist the surgeons. Furthermore, the state-of-the-art robotic-assisted surgeries require intraoperative video images being captured and displayed on the monitors for the surgeons. Consequently, for many surgical procedures, e.g., a gastric sleeve or cholecystectomy, a large cache of surgical videos already exist and continue to be created as a result of a large number of surgical cases performed by many different surgeons from different hospitals.

Surgical videos provide excellent visual feedback to track the usages of surgical tools during laparoscopic surgeries as well as robotic surgeries. Machine-learning tool detection and tracking solutions have been developed to leverage surgical videos to extract useful information, such as detecting which surgical tools have been used and how often each surgical tool has been used during a surgery to enable various clinical applications. Another important use case of surgical videos is to detect improper usage or handling of energy tools/devices that can cause injuries to the patients during surgeries. However, in order to automatically identify improper usage or handling of energy tools/devices, it is necessary to have access to certain energy tool usage data such as "energy tool presence duration" or "energy tool activation duration." While an energy tool can use an internal data logging system to record and maintain certain energy tool usage data, there are a number of drawbacks associated with an internal data logging mechanism. Firstly, the data logs of an energy tool are not easily accessible or available to everyone. Secondly, the data logging function can be accidentally turned off for a surgical procedure, resulting in missing data logs. Thirdly, the data logs from an internal data logging system are often times incomplete and can be susceptible to timing errors so that they can fail to match up with the actual timings of the energy tool use.

Hence, what is needed is a technique for automatically detecting energy tool activations from surgical videos without the need for the internal data logs of the energy tool.

SUMMARY

Embodiments described herein provide various techniques and systems for constructing machine-learning (ML)/deep-learning (DL) energy tool activation detection models (or "activation detection models") for processing surgical videos and generating accurate activation duration estimates and accurate total activation counts from full or portions of surgical videos. This disclosure also provides various techniques and systems for preparing high-quality training dataset used for constructing the disclosed activation detection models. The disclosure additionally provides various techniques and systems for training and validating different configurations of the activation detection models and identifying an optimal activation detection model. The disclosed activation detection model after being properly trained and validated, can detect each activation event of an energy tool within a full surgical video of a surgical procedure or portions of the surgical video corresponding to particular surgical tasks/steps. The disclosed activation detection model can also generate the following activation-related estimations based on the detected activation events: (1) the duration of each detected activation event; and (2) the total number of detected activation events during the full surgical video of the surgical procedure or within a portion of the surgical video corresponding to particular surgical task/step.

In one aspect, a process for detecting energy tool activations is disclosed. The process can begin by receiving a surgical video (e.g., an endoscope video) of a surgical procedure involving energy tool activations, such as a gastric bypass or a sleeve gastrectomy procedure. The process then applies a sequence of sampling windows to the surgical video to generate a sequence of windowed samples of the surgical video. Next, for each windowed sample in the sequence of windowed samples, the process applies a deep-learning model to a sequence of video frames within the windowed sample to generate an activation/non-activation inference and a confidence level associated with the activation/non-activation inference for the windowed sample. As a result, a sequence of activation/non-activation inferences and a sequence of associated confidence levels are generated for the surgical video. The process subsequently identifies a sequence of activation events in the surgical video based on the sequence of activation/non-activation inferences and the sequence of associated confidence levels.

In some embodiments, the process identifies the sequence of activation events by identifying one or more consecutive activation inferences located between two non-activation inferences in the sequence of activation/non-activation inferences as a single activation event in the sequence of identified activation events.

In some embodiments, the process generates a total activation count for the surgical video by incrementing an activation count by one in response to the detection of the one or more consecutive activation inferences. The process outputs the final-updated activation count as the total activation count for the surgical video after processing the sequence of activation/non-activation inferences.

In some embodiments, the one or more consecutive activation inferences include multiple consecutive activation inferences, and the process estimates the duration of the identified activation event by first identifying the first and the last inferences in the multiple consecutive activation inferences that correspond to two partial-activation windowed samples that partially overlap with the identified activation event (i.e., overlapping with the beginning portion and the ending portion of the identified activation event, respectively). Next, the process determines an amount of partial-overlap between each of the two partial-activation windowed samples and the identified activation event based on the two confidence levels associated with the first and the last inferences. The process then computes the duration of the identified activation event as the sum of the two determined amount of partial-overlaps and full overlaps with the identified activation event of other windowed samples between the two partial-activation windowed samples associated with the multiple consecutive activation inferences.

In some embodiments, the process determines the amount of partial-overlap between each of the two partial-activation windowed samples and the identified activation event by multiplying a window length of the sampling windows with the confidence level associated with the first or the last inference.

In some embodiments, the sequence of sampling windows has a common window length determined based on an activation duration distribution of a large number of previously-identified activation events from a large number of surgical videos of the surgical procedure.

In some embodiments, the process sequentially applies the sequence of sampling windows by adding a predetermined amount of overlap between consecutive sampling windows.

In some embodiments, the process further includes steps of deriving an energy tool usage metric by detecting, within the surgical video, an on-screen presence event of the energy tool. For example, the process can detect the on-screen presence event by applying a deep-learning energy-tool presence/absence detection model on the surgical video. The process then superimposes the detected on-screen presence event on the identified sequence of activation events to identify a group of detected activation events within the detected on-screen presence event. The process subsequently outputs an activation momentum metric as the ratio of the number of detected activation events within the group of detected activation events to the duration of the detected on-screen presence event.

In some embodiments, the process further includes the steps of training the deep-learning model. To do so, the process can first receive a group of annotated surgical videos of the surgical procedure. Note that each annotated surgical video in the group of annotated surgical videos includes a set of identified activation events, wherein each identified activation event is annotated with a starting timestamp and an end timestamp. Next, for each annotated surgical video in the group of annotated surgical videos, the process generates a set of labeled training data by sampling the annotated surgical video. The process then adds the set of labeled training data into a training dataset. The process subsequently trains the deep-learning model using the training dataset.

In some embodiments, the process generates the set of labeled training data by sequentially applying a sequence of sampling windows to the annotated surgical video to generate a sequence of windowed samples of the annotated surgical video. Next, for each windowed sample in the sequence of windowed samples, the process acquires a ground truth label for the windowed sample based on the temporal location of the windowed sample with respect to the set of annotated activation events in the annotated surgical video and adds the labeled windowed sample into the set of labeled training data.

In some embodiments, the process acquires the ground truth label for the windowed sample based on the temporal location of the windowed sample by: (1) providing a first integer label of "1" to the windowed sample if the windowed sample is situated entirely inside an annotation activation event within the set of annotated activation events; and (2) providing a second integer label of "0" to the windowed sample if the windowed sample is situated entirely outside of any of the set of annotated activation events.

In some embodiments, the process acquires the ground truth label for the windowed sample by providing a float number label between "0" and "1" to the windowed sample if the windowed sample partially overlaps with an annotated activation event within the set annotated activation events. Note that the float number label is computed based on the percentage of the windowed sample positioned inside the identified activation event.

In some embodiments, the process further includes the steps of: (1) providing a negative sign to the float number label assigned to the windowed sample if the windowed sample overlaps with the beginning portion of the annotated activation event; and (2) providing a positive sign to the float number label assigned to the windowed sample if the windowed sample overlaps with the ending portion of the annotated activation event.

In some embodiments, the process further includes determining whether the center video frame within the windowed sample is inside the annotated activation event. In response to determining that the center video frame is outside of the annotated activation event, the process excludes the windowed sample from the training dataset.

In another aspect, a system for automatically detecting energy tool activations during a surgical procedure is disclosed. The system can include one or more processors and a memory coupled to the one or more processors. Moreover, the memory of the system stores a set of instructions that, when executed by the one or more processors, cause the system to: (1) receive an surgical video of a surgical procedure involving energy tool activations; (2) apply a sequence of sampling windows to the surgical video to generate a sequence of windowed samples of the surgical video; (3) for each windowed sample in the sequence of windowed samples, apply a deep-learning model to a sequence of video frames within the windowed sample to generate an activation/non-activation inference and a confidence level associated with the activation/non-activation inference, thereby generating a sequence of activation/non-activation inferences and a sequence of associated confidence levels; and (4) identify a sequence of activation events based on the sequence of activation/non-activation inferences and the sequence of associated confidence levels.

In yet another aspect, a process for constructing a high-quality training dataset for training an energy tool activation detection model is disclosed. The process can begin by receiving multiple sequences of annotated activation events from a group of annotators independently annotating a surgical video. Note that each sequence of annotated activation events is extracted from each independently annotated surgical video. Next, the process performs a temporal clustering on the multiple sequences of annotated activation events to group annotated activation events in the multiple sequences of annotated activation events into clusters of annotated activation events. Note that each cluster of annotated activation events belongs to the same activation event in the surgical video. The process next computes statistical consensuses for each cluster of the annotated activation events. The process can then output the computed statistical consensuses as ground truth for the associated activation event in the subsequent model building process.

In some embodiments, each sequence of annotated activation events in the multiple sequences of annotated activation events includes a first annotated activation event positioned between two non-activation periods. This first annotated activation event includes an annotated starting timestamp and an annotated end timestamp.

In some embodiments, the process computes the statistical consensuses for each cluster of the annotated activations by computing a first mean value of the set of annotated starting timestamps within the cluster of annotated activation events, and a second mean value of the set of annotated end timestamps within the cluster of annotated activation events.

In some embodiments, prior to outputting the computed statistical consensuses, the process further includes comparing each annotated activation event within the cluster of annotated activation events with the computed statistical consensuses of the cluster of annotated activation events to identify an anomaly within the cluster of annotated activation events. In response to identifying an anomaly associated with an annotated activation event in the cluster of annotated activation events, the process updates the cluster of annotated activation events by replacing the associated annotated activation event with updated annotations of the associated activation event to eliminate the anomaly.

In some embodiments, wherein after updating the cluster of annotated activation events, the process recomputes statistical consensuses for the cluster of the annotated activation events. As a result, the process outputs the recomputed statistical consensuses as ground truth for the associated activation event in the subsequent model building process.

BRIEF DESCRIPTION OF THE DRAWINGS

The structure and operation of the present disclosure will be understood from a review of the following detailed description and the accompanying drawings in which like reference numerals refer to like parts and in which:

FIG. 16 shows Table 1 which is the summary of model validation results of 12 activation detection models trained with different model parameters and evaluated using the same validation dataset in accordance with some embodiments described herein.

FIG. 17 shows Table 2 which is an exemplary energy dosage table compiled for 20 sleeve gastrectomy cases including both tool activation and tool presence statistical metrics in accordance with some embodiments described herein.

DETAILED DESCRIPTION

Figure 1:
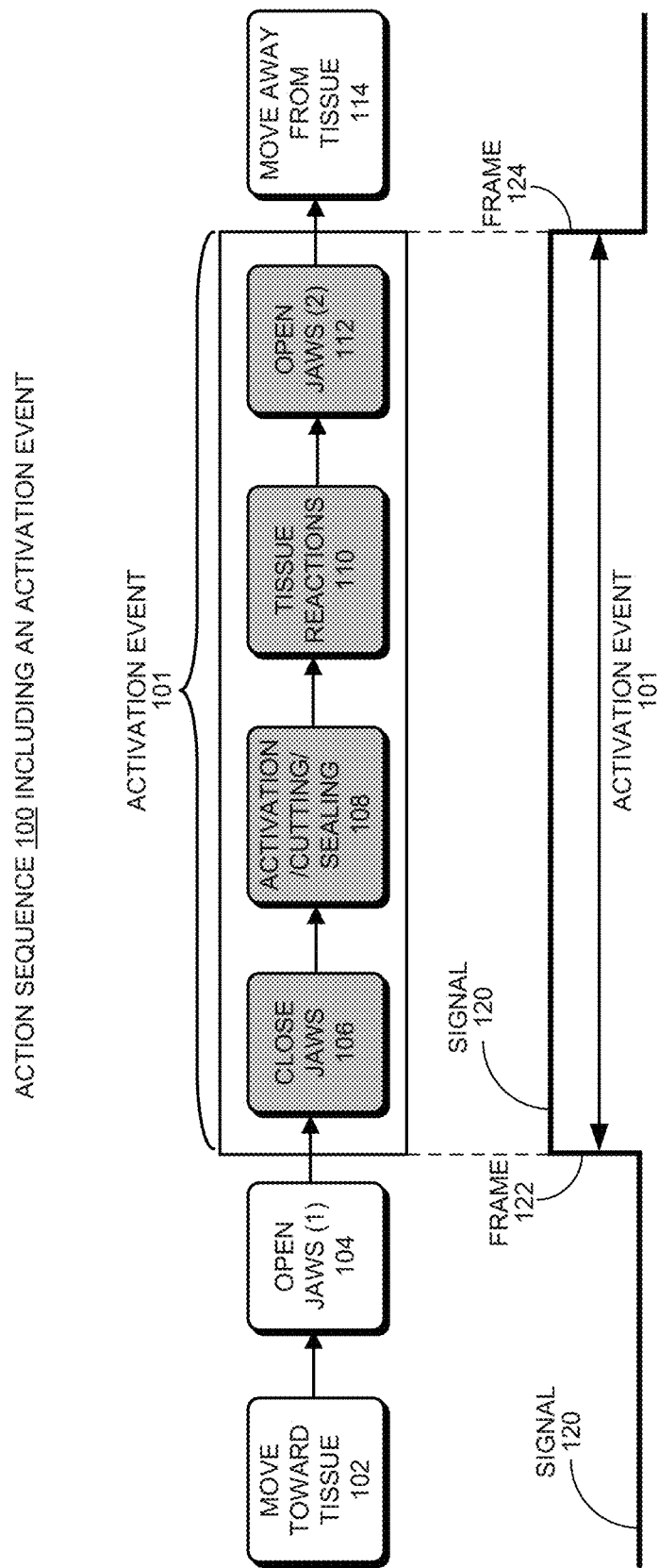
FIG. 1 illustrates an action sequence that generally specifies an energy tool activation event and the actions immediately before and after the activation event in accordance with some embodiments described herein.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, the subject technology is not limited to the specific details set forth herein and may be practiced without these specific details. In some instances, structures and components are shown in block diagram form in order to avoid obscuring the concepts of the subject technology.

Terminology

Throughout this patent disclosure, the terms "energy tool" and "energy device" are used interchangeably to refer to a surgical tool designed to deliver energy (e.g., through electrical or ultrasonic means) to a tissue at a surgical site. Moreover, the terms "energy tool activation event," "tool activation event," "activation event" and "activation" are used interchangeably to refer to a single activation and energy application of an energy tool/device. Furthermore, the terms "deep-learning energy tool activation detection model," "energy tool activation detection model," and "activation detection model" are used interchangeably to refer to the disclosed deep-learning model for detecting occurrences of energy tool activation events.

Overview

Generating a deep-learning model for energy tool activation detection presents a unique set of modeling challenges. It has been observed that the activation events are typically very short in durations, which means that the "input video clips/samples" to the model has to be short. However, short samples can also cause false positives for the model. Secondly, an activation event generally does not represent any significant physical motion. This is because the nature of energy activation is about fixating the energy tool on a certain area of a tissue and applying steady energy on the part of the tissue. As a result, it would be difficult to create a model that is primarily designed to extract temporal features from an input video clip. Thirdly, camera-motion can make the energy tool to appear to be moving, while the tool is generally stationary during an activation event. The false tool motion during an activation event can be interpreted as a non-activation event of the tool, and hence can cause false negatives for a model. Moreover, tool occlusion during an activation event presents a challenge to the model. Note that the occlusion of the energy tool during an activation event can be caused by a number of reasons, which include but are not limited to: (1) occlusion by other surgical tools in the frames: (2) occlusion by the tissue under the operation; (3) occlusion by the blood that may immerse the jaws of the tool; and (4) occlusion by the surgical smoke that can make the scene foggy and difficult to see. Furthermore, it is understood that energy tool action before an activation event (i.e., tool moving toward the targeted tissue) and the action after the activation event (i.e., tool moving away from the targeted tissue) are very different from the activation action itself. This means that any minor inaccurate annotation of the training data can introduce notable noise and have a significant impact on the performance of the model. The disclosed activation detection models are designed to overcome the above-mentioned challenges.

Embodiments described herein provide various techniques and systems for constructing machine-learning (ML)/deep-learning (DL) energy tool activation detection models (or "activation detection models") for processing surgical videos and generating accurate activation duration estimates and accurate total activation counts from full or portions of surgical videos. This disclosure also provides various techniques and systems for preparing high-quality training dataset used for constructing the disclosed activation detection models. The disclosure additionally provides various techniques and systems for training and validating different configurations of the activation detection models and identifying an optimal activation detection model. The disclosed activation detection models after being properly trained and validated, can detect each activation event of an energy tool within a full surgical video of a surgical procedure or portions of the surgical video corresponding to particular surgical tasks/steps. The disclosed activation detection models can also generate the following activation-related estimations based on the detected activation events: (1) the duration of each detected activation event; and (2) the total number of detected activation events during the full surgical video of the surgical procedure or within a portion of the surgical video corresponding to particular surgical task/step.

In various embodiments, the disclosed activation detection models detect activation events within a surgical video using a sequence of sampling windows of a predetermined window length and a predetermined stride/overlap between adjacent windows, which divides up the surgical video into a sequence of windowed samples/videos clips. The disclosed activation detection models are configured to generate a prediction/classification on each segmented video sample/clip as either an activation event (i.e., an activation inference) or a non-activation event (i.e., a non-activation inference), and a confidence level associated with the activation/non-activation inference. In some embodiments, the predetermined window length is selected to be smaller than most of the known activation durations so that each activation event can be represented by multiple windowed samples. Hence, based on the model prediction outputs, each activation event within the surgical video can be identified as either a single windowed sample that acquired an activation inference between two non-activation inferences, or multiple consecutive windowed samples that acquired activation inferences between two non-activation inferences.

In some embodiments, the disclosed activation detection models are constructed to identify both windowed samples that are positioned fully inside the activation events, and those windowed samples that are only partially overlap with the activation events. In some embodiments, these partially-overlapping samples, also referred to as "partial activation samples," can be identified as the first and the last windowed samples in the multiple consecutive windowed samples receiving activation inferences. Moreover, the confidence level associated with each identified partial activation sample can be configured to represent the amount of the overlap (e.g., in terms of the percentage of the window length) with a detected activation event. As such, the duration of each detected activation event can be predicted based on the corresponding one or multiple consecutive activation inferences and the corresponding set of confidence levels.

Note that prior to constructing the disclosed activation detection models, a high quality training dataset has to be prepared. In some embodiments, preparing a high-quality training dataset for training activation detection models involves a two-level surgical video annotation and labeling procedure based on a group of raw surgical videos. Specifically, in the first level of the surgical video annotation and labeling procedure, each activation event occurred in each raw surgical video is identified and annotated by a group of independent annotators/experts, such as a group of surgeons. Note that each annotated activation event includes an identified starting timestamp (i.e., the beginning) and an identified stopping timestamp (i.e., the end) of an identified activation event. As a result, each annotated activation event also generate the duration of the identified activation event. Next, the statistical consensuses of each identified activation event annotated by the group of independent annotators are computed, e.g., by computing a first mean value of the set of starting timestamps of the identified activation event, and a second mean value of the set of stopping timestamps of the same identified activation event. Generally speaking, the statistical consensuses can be used as the ground truth labels for the identified activation event.

In some embodiments, prior to computing the statistical consensuses, a temporal clustering is applied to multiple sequences of annotated activation events by the group of annotators to group those annotated activation events belonging to the same activation events into clusters, e.g., based on temporal similarities of the annotated activation events by different annotators. In some embodiments, after computing the statistical consensuses for a given annotated activation event, individual annotations of the given activation event can be compared with the computed statistical consensuses of the given activation event to identify any anomaly in the individual annotations. If an anomaly is detected for an individual annotation of the given activation event, the faulty annotation is reviewed and refined by the responsible annotator and replaced by an updated annotation of the given activation event. After all of the detected anomalous annotations have been reviewed and corrected, the statistical consensuses for the given annotated activation event is updated based on the updated group of individual annotations. The updated/refined statistical consensuses are then used as the ground truth labels for the given activation event.

In some embodiments, in the second level of the surgical video annotation and labeling procedure, each annotated surgical video outputted from the first level of the annotation and labeling procedure is sampled using a sequence of sampling windows of a predetermined window length and a predetermined stride/overlap between adjacent windows, which then generates a sequence of windowed samples/videos clips of the annotated surgical video. Note that the predetermined window length selected for labeling the annotated surgical video can be identical to the predetermined window length used by the trained activation detection model for processing and detecting activation events in surgical videos. Next, for each windowed sample/video clip in the sequence of windowed samples applied to the annotated surgical video, the temporal location of the windowed sample with respect to the annotated activation events in the annotated surgical video is determined.

Specifically, (1) when the windowed sample is determined to be fully inside a determined non-activation period, a ground truth label 0.0 is assigned to each frame within the windowed sample; (2) when the windowed sample is determined to be fully inside an annotated activation event, a ground truth label 1.0 is assigned to each frame within the windowed sample; (3) when the windowed sample is determined to partially overlap with the leading portion of an annotated activation event, a float number between 0.0 and 1.0 with a negative sign and a value equal to the percentage of overlap with the annotated activation event is assigned to each frame within the windowed sample; and (4) when the windowed sample is determined to partially overlap with the ending portion of an annotated activation event, a float number between 0.0 and 1.0 with a positive sign and a value equal to the percentage of overlap with the annotated activation event is assigned to each frame within the windowed sample. Finally, the labeled windowed samples generated from an ensemble of annotated surgical videos form a training dataset for training and validating the disclosed activation detection models. A person skilled in the art can readily appreciate that the disclosed surgical video annotation and labeling procedure for preparing the high-quality training dataset for training and validation activation detection models mirrors the disclosed activation event inference procedure when applying the trained activation detection model on a raw surgical video.

The disclosed activation detection models can be used to infer and detect each and every energy tool activation event in a surgical video, such as an endoscope video or a laparoscopy video and subsequently extract both the duration of each detected activation event and the total count of the detected activation events. Note that from the two basic types of energy tool activation measurements and estimates directly outputted by the disclosed activation detection models, additional energy tool usage metrics can be derived which can provide additional insights into surgical techniques and skills, as well as case complexity. These basic and derived energy tool usage metrics can be used to understand and therefore regulate the applied energy dose, thereby increasing the sealing quality of the target tissues, and reducing the damage to the surrounding healthy tissues. In other words, these energy tool usage metrics can facilitate a surgeon at a portfolio-level to understand the differences in his/her own device choice across his/her own cases as well as other surgeons' cases. For example, these basic and derived energy tool usage metrics can facilitate a surgeon to determine how often he/she uses a particular energy tool compared with other surgeons.

It is understood that there exists wide variations in terms of what and how energy tools are used in the same procedure and steps. These variations can lead to clinically significant differences in surgical outcomes. As a result, capturing these variations can provide a platform to study and identify the optimal techniques of energy tool usage that can improve tool use efficiency and patient outcomes. The disclosed activation detection models are applicable to a wide variety of energy tools including bipolar and ultrasonic energy tools, and different energy tool models such as Harmonic™, LigaSure™, Enseal™, Sonicision™. Hence, the basic and derived energy tool usage metrics of the disclosed activation detection models can be used to capture these variations and to better understand the value of certain techniques given these wide variations. For example, an accumulated activation duration of an energy tool (either during the entire surgery or particular surgical tasks/steps) can be used as an indicator for the level of efficiency of the energy tool itself and/or the skill of the surgeon performing the surgery. As another example, the total number of activations of the energy tool (either during the entire surgery or particular surgical tasks/steps) can be used as an indicator of a skill level of the surgeon performing the surgery and/or a complexity level of the surgery.

Surgical Video Collection, Annotation and Augmentation

Surgical videos including both laparoscopic surgery videos and robotic surgery videos captured during minimally invasive surgeries can help to improve both the efficiency and the quality of the surgeries by providing real-time visual feedback. Object detection models and techniques can leverage this visual feedback by extracting and analyzing information from a surgical video, such as detecting which surgical tools are used to enable various clinical use cases. In this disclosure, a deep-learning-based model and technique for processing a surgical video to detect each and every energy device (e.g., a Harmonic™ vessel sealer manufactured by Ethicon™) activation event in each and every surgical task/step throughout a surgical procedure captured in the surgical video is disclosed.

In some embodiments, prior to training the disclosed energy tool activation detection model, laparoscopy surgical videos of surgical procedures involving one or more energy tools, e.g., a Harmonic™ vessel sealer, a Enseal™ vessel sealer, a LigaSure™ vessel sealer, or a Sonicision™ vessel sealer, are collected in the data collection phase. In some embodiments, these surgical videos are collected from both gastric bypass and sleeve gastrectomy procedures. The collected videos are then independently labeled by a number of annotators (e.g., at least 4 individuals) who are highly skilled and sufficiently trained in annotating such surgical videos and energy tool activation events within these surgical videos.

FIG. 1 illustrates an action sequence 100 that generally specifies an energy tool activation event 101 (or "activation event") and the actions immediately before and after activation event 101 in accordance with some embodiments described herein. As can be seen in FIG. 1, action sequence 100 containing a single energy tool activation event 101 is composed of a sequence of steps/actions in temporal order is as follows: (1) the tool moving toward the tissue action 102, or "move toward tissue" (step) 102; (2) opening the jaws of the energy tool action 104, or "open jaws" (step) 104; (3) closing the jaws of the energy tool action 106, or "close jaws" (step) 106; (4) activating/energizing the tool and tissue cutting/sealing actions 108, or "activation/cutting/sealing" (step) 108; (5) surgical smoke and other tissue reaction reactions 110, or "tissue reactions" (step) 110; (6) opening the jaws of the energy tool action 112, or "open jaws" (step) 112; and finally (7) the tool moving away from the tissue action 114, or "move away from tissue" (step) 114. Note that within action sequence 100, close jaws step 106, activation/cutting/sealing step 108, tissue reactions step 110, and open jaws step 112 collectively form the single activation event 101.

FIG. 1 also shows an exemplary signal representation 120 of action sequence 100. As can be seen, activation event 101 is represented with a high signal level (e.g., using a numerical value 1) in signal representation 120, whereas durations outside of activation event 101 are represented with a low signal level (e.g., using a numerical value 0) in signal representation 120. As a result, activation event 101 is defined by a starting video frame 122 and an end video frame 124 which correspond to the moment when the jaws are closed around a tissue and the moment when the jaws open up to release the tissue, respectively. Note that signal representation 120 represents an ideal output of the disclosed activation detection model when the model is applied to the video clip depicting action sequence 100. However, before the activation detection model can be used for activation inferences, the model needs to be taught (i.e., trained) to recognize different actions/steps involves in an activation event, particularly the actions of closing the jaws (i.e., step 106) and opening the jaws (e.g. step 112). Moreover, the activation detection model needs to be taught (i.e., trained) to distinguish similar actions/steps that may or may not belong to an activation event, e.g., between the actions of opening the jaws 104 and opening the jaws 112. This requires constructing a high quality training dataset from a collection of surgical videos, wherein constructing the training dataset begins with accurately annotating each surgical video.

Specifically, annotating a surgical video in preparation for constructing a training dataset generally includes the steps of: (1) identifying each and every energy tool activation event depicted in the surgical video; and (2) for each identified activation event (e.g., activation event 101 in FIG. 1), further identifying the starting timestamp (e.g., timestamp of starting frame 122 in FIG. 1) and the stopping timestamp (e.g., timestamp of end frame 124 in FIG. 1) of the activation event. Because each activation event generally lasts for about a few seconds, the resolution used for annotating the starting timestamp and the stopping timestamp can be set to milliseconds (ms). For example, the following is an exemplary annotated activation event by a particular annotator: [starting timestamp: 00:54:45.008 sec; stopping timestamp: 00:54:45.904 sec]. As another example, an annotated activation event having a longer activation duration receives the following timestamps: [starting timestamp: 01:06:22.551 sec; stopping timestamp: 01:06:26.197 sec].

Figure 2:
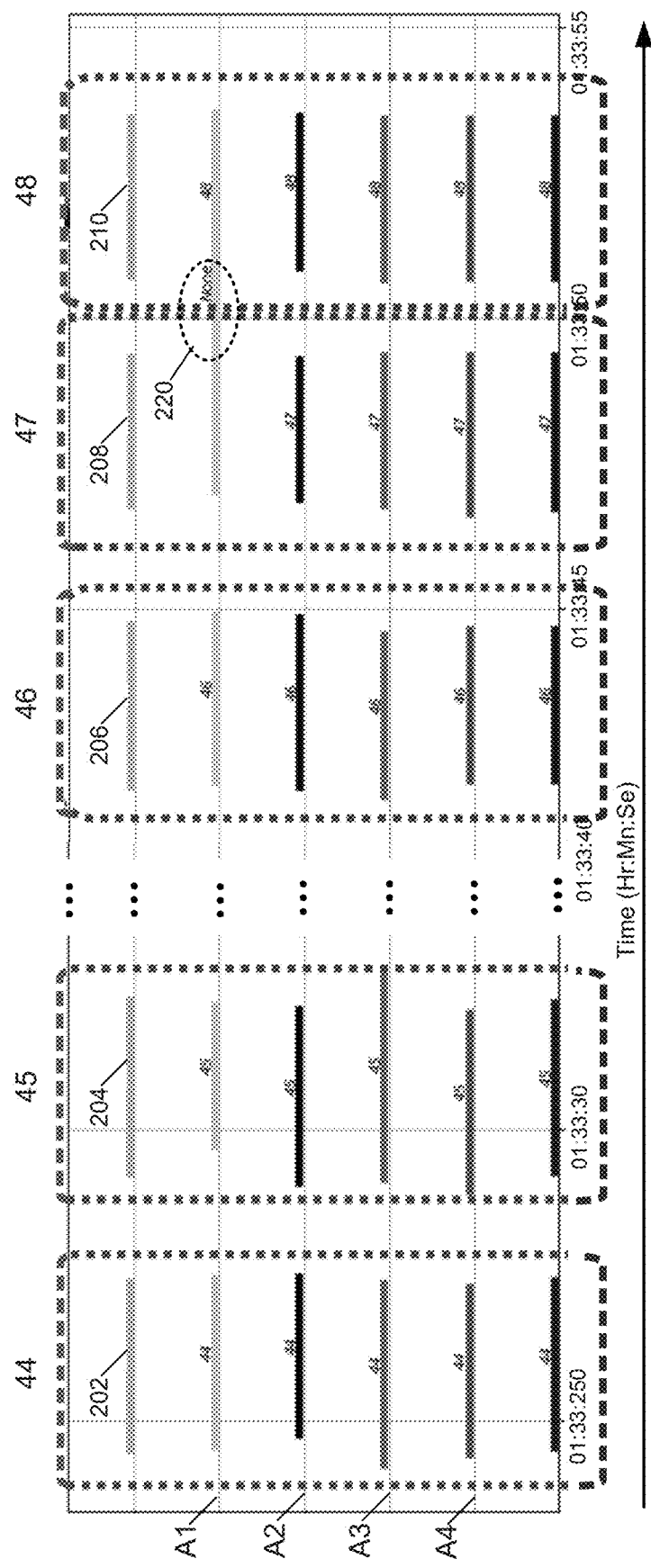
FIG. 2 illustrates an exemplary activation clustering process on a segment of a given surgical video annotated by a group of annotators in accordance with some embodiments described herein.

Referring back to FIG. 1, note that identifying the boundary frames 122 and 124 of activation event 101 can be subjective and as a result the identified timestamps of the same activation event can differ from one annotator to another annotator. Moreover, it is also possible that one annotator in the group of annotators fails to identify one of two boundaries of a given activation event. In some embodiments, to mitigate annotation discrepancies among the group of annotators, after the group of annotators has individually annotated a given surgical video, the annotated activation events from the group of annotators are clustered based on their temporal associations. In other words, a temporal clustering process is used to identify and group the same activation event annotated by the group of annotators. FIG. 2 illustrates an exemplary activation clustering process 200 on a segment of a given surgical video annotated by a group of annotators in accordance with some embodiments described herein. As can be observed in FIG. 2, a sequence of five activation events with identification (ID) number 44-48 have been independently annotated by a group of 4 annotators A1-A4 to generate four sequences/sets of annotated activation events (i.e., the 4 middle rows in FIG. 4). Note that each annotated activation event by a given annotator is represented by a horizontal bar defined by a starting timestamp and a stopping timestamp. Next, a temporal clustering model can be applied to the 4 sequences of annotation results to automatically associate multiple annotated activation events of the same activation event but in different annotated sequences into a "cluster." For example, the automatic clustering model can be configured to determine the correct associations by searching the neighborhood of each annotated activation event. The exemplary results of the clustering process showed five identified clusters corresponding to the five annotated activation events 44 to 48.

In some embodiments, after generating the clusters of the annotated activation events, statistical consensus (or "consensus") for each cluster of the annotated activation events is computed. For example, the computed consensus can include a first mean value of the set of starting timestamps associated with the cluster of annotated activations, and a second mean value of the set of stopping timestamps associated with the cluster of annotated activations. Naturally, the consensus for the duration of the associated activation event can be obtained as the difference between the first mean value and the second mean value. The five computed consensus for the five activation events 44 to 48 are represented by the five temporal bars 202-210 in the first row of FIG. 2. Once the consensus for an annotated and clustered activation event has been determined, they can be used to compare with each individual annotation within the given cluster to identify anomalies. In some embodiments, if an individual annotated event is significantly different in one or both of the timestamps from the consensus, an anomaly will be reported. Note that the anomaly detection threshold can be set either using an absolute value, e.g., ~200 ms as the maximum allowable difference, or using a percentage value, e.g., ~10% as the maximum allowable percentage difference.

For example, when using 200 ms as the anomaly detection threshold, an annotated activation event by a first annotator having the computed differences of (−0.066 sec, 0.011 sec) from the consensus is considered a quality annotation, because both timestamps of the annotated event differ from the respective consensus values less than 200 ms. In contrast, another annotation of the same activation by a second annotator having the computed differences of (0.284 sec, −0.046 sec) is considered to include an anomaly, because the starting timestamp of this annotated event differs from the starting-timestamp consensus more than 200 ms. Yet another annotation of the same activation by a third annotator having the computed differences of (−0.018 sec, 0.359 sec) is also considered to include an anomaly, because the stopping timestamp of this annotated event differs from the stopping-timestamp consensus more than 200 ms. Note that using the consensus comparisons on individual annotations can also identify the aforementioned anomaly when a given annotator completely fails to identify one or both of the boundaries of the associated activation event. In such cases, one or both of the computed differences with the consensus will have invalid values.

Note that FIG. 2 also shows another type of annotation error 220 in the second row corresponding to annotation results by annotator A1. Specifically, annotator A1 fails to identify both the stopping timestamp for activation event 47 and the starting timestamp for activation event 48. Instead, activation events 47 and 48 are identified by annotator A1 as a single activation event. However, this type of annotation error can be detected during the annotation clustering process when the clustering model fails to find any association for either the starting timestamp or the stopping timestamp of activation event 48 annotated by A1. Alternatively, the above anomalies can be identified when the computed differences with the consensus include invalid values.

In any of the above-described scenarios, when an anomaly is detected in one or both timestamps of a given annotated activation event, the individual annotator responsible for the faulty annotation is required to review and refine the give annotation, i.e., to carefully redo the annotation on the given activation event. In some embodiments, after all of the detected faulty annotations have been corrected and/or refined, the statistical consensuses for those clustered activation events including updated annotations can be recomputed to generate updated statistical consensuses. Generally speaking, an updated statistical consensus of a cluster of annotated event including updated annotations has improved accuracy over the original statistical consensus of the cluster of annotated event without updated annotations. Next, individual annotations including the updated annotations within a cluster can be again compared with the updated statistical consensus, and the above-described annotation-anomaly detection and correction procedure can be repeated. When individual annotations within a given cluster no longer contain anomalies, the final statistical consensus for the cluster of annotations can be output as the ground truth for the associated activation event in the subsequent model building process.

In some embodiments, the updated statistical consensus of each annotated activation event can be further reviewed with even a greater degree of thoroughness by AI data analytics professionals, and final adjusted statistical consensus by the data analytics professionals is used as the ground truth for the associated activation event in the subsequent model building process. Note that the above-described surgical video annotation procedure, when applied to a raw surgical video, generates an annotated video that annotates the beginning and the end of each and every activation event in the video with extremely high accuracy. Hence, the disclosed surgical video annotation procedure can make significant impact on the overall quality of the disclosed activation detection model which is trained on a training data extracted from the annotated videos.

Figure 3:
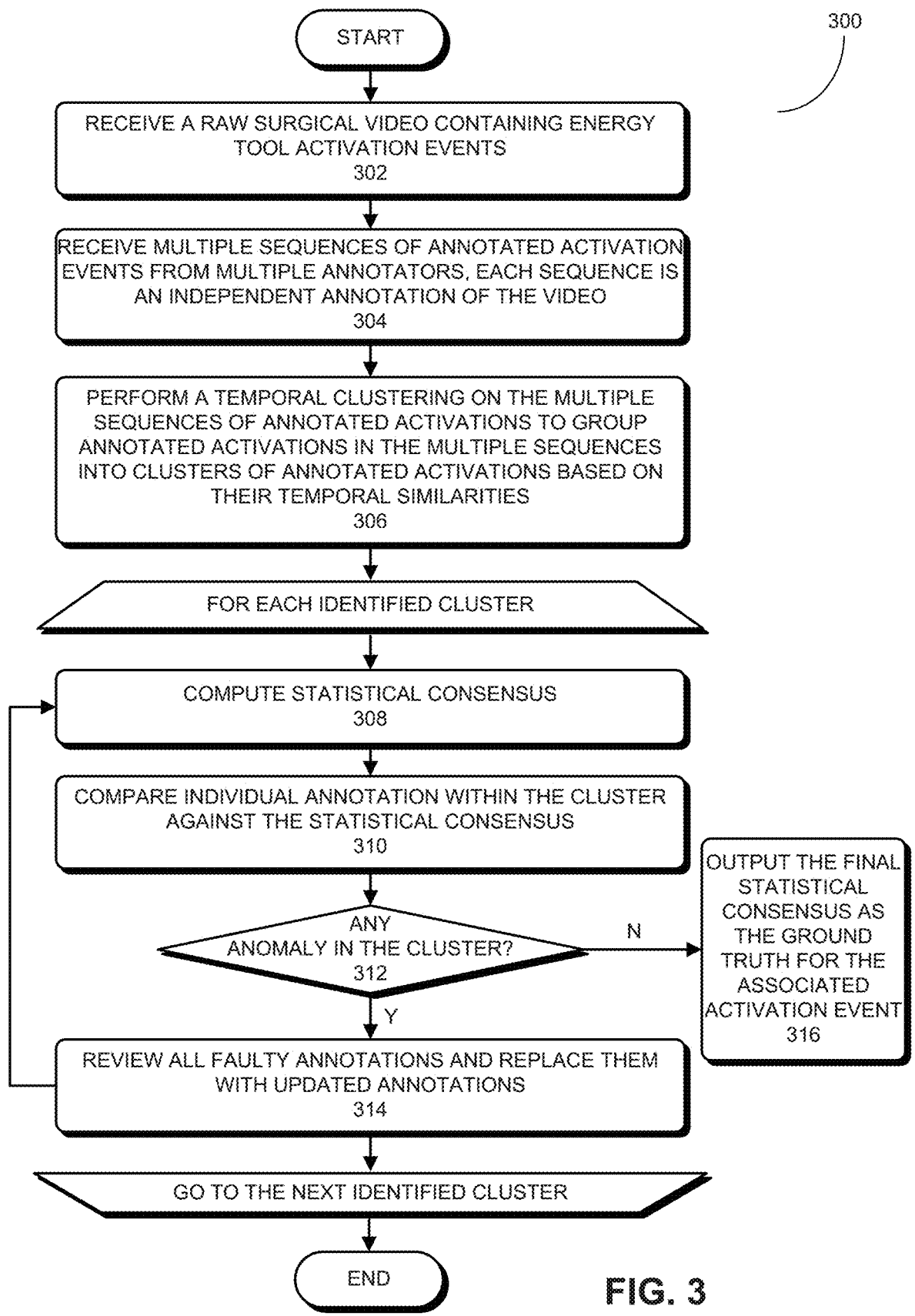
FIG. 3 presents a flowchart illustrating a process for annotating a raw surgical video containing energy tool activation events in preparation for constructing a training dataset for the disclosed activation detection model in accordance with some embodiments described herein.

FIG. 3 presents a flowchart illustrating a process 300 for annotating a raw surgical video containing energy tool activation events in preparation for constructing a training dataset for the disclosed activation detection model in accordance with some embodiments described herein. In one or more embodiments, one or more of the steps in FIG. 3 may be omitted, repeated, and/or performed in a different order. Accordingly, the specific arrangement of steps shown in FIG. 3 should not be construed as limiting the scope of the technique.

Process 300 may begin by receiving a raw surgical video containing energy tool activation events (step 302). In some embodiments, the raw surgical video is a recorded gastric bypass procedure or sleeve gastrectomy procedure. Process 300 next receives multiple sequences of annotated activation events from a group of annotators independently annotating the raw surgical video, wherein each sequence of annotated activation events is extracted from each independently annotated surgical video (step 304). In some embodiments, each annotated activation event in a given sequences of annotated activation events includes an identified starting timestamp and an identified stopping timestamp of an identified activation event. Next, process 300 performs a temporal clustering operation on the multiple sequences of annotated activation events to group those annotated activation events in the multiple sequences of annotated activation events into clusters of annotated activation events based on their temporal similarities, wherein each cluster belongs to the same activation event in the surgical video (step 306).

Next, for each identified cluster of the annotated activation events, process 300 computes statistical consensus (or "consensus") for the cluster of the annotated activations (step 308). For example, the computed consensus can include a first mean value based on the set of starting timestamps associated with the cluster of annotated activations, and a second mean value of the set of stopping timestamps associated with the same cluster of annotated activations. Next, process 300 compares each individual annotation within the given cluster against the statistical consensus (step 310) to determine if there are anomalies in the given cluster (step 312). For example, an anomaly is identified if an individual annotation is different from a consensus more than a threshold value (e.g., 200 ms) or if an attempt to compare against a consensus yields an invalid value. If an anomaly is detected for an individual annotation in the given cluster, the faulty annotation is reviewed and refined by the responsible annotator and replaced by an updated annotation (step 314). After all of the detected faulty annotations have been reviewed and corrected, process 300 can return to step 308 to compute updated statistical consensuses based on the updated annotations and annotation-anomaly detection and correction steps 310-314 can be repeated. When individual annotations within a given cluster not longer contain anomalies, process 300 outputs the final statistical consensus for the cluster of annotated activations as the ground truth for the associated activation event in the subsequent model building process (step 316). Note that steps 308-316 of process 300 are also looped over all identified clusters associated with all of the identified and annotated activation events to generate an annotated surgical video containing the ground truths for all of the identified activation events.

By applying the above-described surgical video annotation processes and techniques to a collection of raw surgical videos, we obtain an ensemble of accurately annotated surgical videos containing the ground truths for the activation events within these surgical videos. In some embodiments, before generate a training dataset for the activation detection model from the annotated surgical videos, the annotated surgical videos can be first divided into a first group of training videos, a second group of validation videos, and a third group of test videos. For example, an ensemble of annotated surgical videos may be split into a first group of 75% videos for the model training process, a second group of 15% videos for the model validation process, and a third group of 10% videos for final model test process. After dividing the annotated surgical videos into the separate groups of training, validation and test videos, a proposed window-based training dataset generation procedure can be applied to each annotated video in each separate group of training, validation, or test videos. Note that dividing the annotated surgical videos into the respective groups before sampling each annotated video and generating labeled samples allows for separating the training dataset, the validation dataset, and the test dataset early on at a higher level (i.e., at the video level) so that the later-generated labeled video clips/samples are automatically separated into the designated training dataset, the validation dataset, and the test dataset. We now describe the proposed window-based training dataset generation processes and techniques, which can be equally applicable to any annotated surgical video assigned to any group of training, validation, or test videos.

Figure 4:
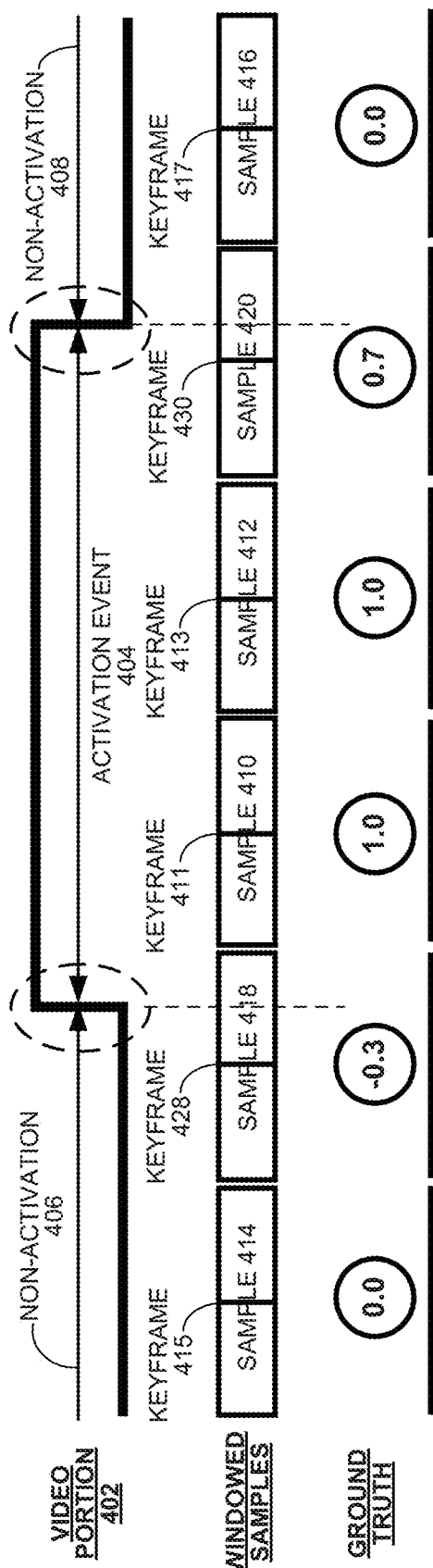
FIG. 4 shows an exemplary procedure of generating labeled samples/video clips based on an annotated surgical video in accordance with some embodiments described herein.

In some embodiments, a disclosed window-based training dataset generation procedure uses a window-based approach, i.e., by sequentially applying a sampling window of a predetermined window length to each annotated video to segment and convert the annotated video into a sequence of video clips (also referred to as "windowed samples" or simply "samples" or "clips" below), wherein each video clip has a duration equal to the predetermined window length. In some embodiments, after an annotated surgical video has been converted into the sequence of windowed samples/video clips, a ground true label is generated for each sample/video clip to define each sample/video clip as either being a part of an activation event or being a part of a non-activation period. In some embodiments, the equal-length sampling windows can be applied to an annotated surgical video end-to-end without overlap as illustrated in FIG. 4. However, as will be described below, the sequence of sampling windows can also be applied to an annotated video with stride that is less than the window length, so that the adjacent sampling windows overlap each other.

FIG. 4 shows an exemplary procedure of generating labeled samples/video clips based on an annotated surgical video in accordance with some embodiments described herein. Specifically, the first row of FIG. 4 represents a video portion 402 of the annotated surgical video that is composed of an annotated activation event 404 represented by a high signal level (e.g., a pulse) and positioned between two short non-activation periods 406 and 408, represented by a low signal level. Moreover, the second row of FIG. 4 represents applying a sequence of end-to-end sampling windows to the video portion 402 of the annotated surgical video. In the particular example shown, it is noted that the annotated activation event 404 can contain multiple of the applied windowed samples. It can also be observed that, in addition to a first type of samples 410 and 412 which fall completely inside the annotated activation event 404, there are two other types of samples: non-activation samples 414 and 416 that are located fully inside non-activation periods 406 and 408; and samples 418 and 420, which partially overlap with annotated activation event 404. We refer samples 418 and 420 which partially overlap with an activation event as "partial activation samples."

In some embodiments, to generate ground truth labels for the windowed samples for the subsequent model training process, the first type of samples, such as samples 410 and 412 that are positioned fully inside an activation event, are labeled as 1.0. The second type of samples, such as samples 414 and 416 that are positioned fully outside of any activation event, i.e., fully inside non-activation periods of the annotated surgical video, are labeled as 0.0. These two types of ground truth labels are shown in the third row in FIG. 4. In some embodiments, for the third type, i.e., the partial activation samples such as samples 418 and 420, a floating point number (also referred to as "float number" below) between 0.0 and 1.0 are assigned to such samples, and the exact values assigned to such samples would depend on the amount of overlaps between such samples and the corresponding activation events. For example, sample 418 receives a float number 0.3 as the ground truth label because the corresponding sampling window has a 30% overlap with activation event 404, whereas sample 420 receives a float number 0.70 as the ground truth label because the corresponding sampling window has a 70% overlap with activation event 404.

However, even though both samples 418 and 420 include partial activations, they should be further differentiated from each other because sample 418 begins in non-activation period but ends inside the activation event, whereas sample 420 begins inside the activation event but ends in another non-activation period. More specifically, sample 418 includes the starting timestamp of the activation event (also referred to as "the first type of partial activation"); whereas sample 420 includes the stopping timestamp of the activation event (also referred to as "the second type of partial activation"). Note that in terms of surgical action, the first type of partial activation includes the moment when the two jaws of the energy tool close on a tissue, i.e., close jaws 106 in FIG. 1; whereas the second type of partial activation includes the moment when the two jaws of the energy tool open up to release the tissue, i.e., close jaws 112 in FIG. 1. To facilitate the activated detection model to learn and differentiate these two types of partial activation, a negative sign can be provided to the float number 0.3 assigned to sample 418 to indicate the first type of partial activation, while the float number 0.7 assigned to sample 420 can maintain the positive sign to indicate the second type of partial activation. These float number types of ground truth labels for the partial activation samples are also shown in the third row in FIG. 4. A person skilled in the art would appreciate that in other embodiments, the signs to the float numbers assigned to the first type of partial activation and the second type of partial activation can be reversed without departing from the scope of the disclosure. Note that while it is possible to label the two types of partial activation samples 418 and 420 without providing signs to the float number labels, further distinguishing these two types of samples with different signs clearly helps to generate more accurate activation detection models.

Note that after a given annotated surgical video has been segmented into a sequence of windowed samples/video clips (either with or without overlaps) and ground truth labels have been provided to the sequence of windowed samples, the labeled sequence of windowed samples can be added into a labeled dataset to be combined with other labeled video clips generated from other annotated surgical videos. After the labeled dataset has been constructed for a collection of annotated surgical videos, the ensemble of labeled windowed samples generated from the collection of annotated surgical videos can then be divided into a training dataset, a validation dataset, and a test dataset. Note that in each of the training, validation, and test datasets, the order of each windowed sample in the original sequence of windowed samples, as well as the association of each windowed sample to the source video have not been maintained. In other words, the labeled sequence of windowed samples corresponding to a given annotated surgical video can be randomly scrambled in each of the training, validation, and test datasets.

In some embodiments, how a given windowed sample receives its ground truth label is based on a representative frame inside the windowed sample, referred to as the "keyframe" of the corresponding video clip. More specifically, to determine the label for the windowed sample, the keyframe within the video clip is first identified. In various embodiments, the location of the keyframe within the video clip can have different choices, wherein different choices of keyframe locations can have different effects on the trained activation detection model. In a particular embodiment, the keyframe can be selected as a center frame within the video clip. However, as will be discussed below, the keyframe can also be selected as the leading frame on the left of the video clip, or the end frame on the right of the clip. We describe below the steps of generating ground truth labels for windowed samples based on the center keyframe scheme. However, the described steps are equally applicable for generating ground truth labels when other keyframe schemes (e.g., the left or the right) selected in place of the center keyframe scheme.

Once the center keyframe within a given windowed sample is identified, e.g., the 10th-frame of a 1.9-sec video clip from a 10 frame-per-second (FPS) video, the ground truth label for the given windowed sample can be determined in three steps. First, the location of the center keyframe with respect to the identified activation events within the annotated video is determined. Next, the identified location of the center keyframe is used to acquire the label for the given windowed sample based on the above described ground truth assignment schemes. Finally, the acquired label for the keyframe is applied to the entire windowed sample as the ground truth label for the windowed sample. For example, the center keyframes 411 and 413 in samples 410 and 412 are determined to be inside activation event 404, and therefore received the label of 1.0. In contrast, the center keyframes 415 and 417 in samples 414 and 416 are determined to be within the non-activation periods, and therefore received the label of 0.0. As a result, samples 410 and 412 received the label of their corresponding center keyframes 411 and 413, i.e., 1.0, whereas samples 414 and 416 received the label of their corresponding center keyframes 415 and 417, i.e., 0.0.

Note that the process of generating ground truth labels for the windowed samples based on the acquired labels of the corresponding keyframes becomes more complex for partial activation samples 418 and 420. For example, center keyframe 428 in sample 418 is within the non-activation period, and therefore would receive the label of 0.0, whereas center keyframe 430 in sample 420 is within activation event 404, and therefore would receive the label of 1.0. However, as discussed above, to teach the model to distinguish these partial activation samples from fully activation samples and non-activation samples, we provide float number labels to these partial activation samples based on the amount of overlaps between such samples and the corresponding activation events. As a result, the keyframes within these partial activation samples may not be used to acquire ground truth labels for these windowed samples. Instead, a partial activation sample can be assigned with a ground truth label based on the amount of overlap with the activation event and the type of the partial activation sample (i.e., the first type or the second type). However, the keyframe within the partial activation sample can play the role of a hyperparameter in the model training process to decide on whether the partial activation sample to be include or exclude in the model training process.

More specifically, the location of the keyframe of a partial activation sample with respect to an annotated activation event can be used to determine whether the partial activation sample should be considered as a part of the annotated activation event. Generally speaking, only those partial activation samples whose keyframes are located inside an annotated activation event are considered as a part of the activation event. For example, in the exemplary activation event 404, partial activation sample 420 (along with samples 410 and 412) is used to represent activation event 404 because its keyframe 430 is inside activation event 404 (assuming center keyframe is used). However, partial activation sample 418 is excluded from representing activation event 404 because its center keyframe 428 is outside of activation event 404, even though sample 418 partially overlaps activation event 404. In some embodiments, when a partial activation sample (e.g., sample 418) is excluded from representing a corresponding activation event (e.g., activation event 404), the partial activation sample is excluded from the training dataset for training the activation detection model.

In some embodiments, the decision on whether to include or exclude a windowed sample from the model training process is made based on a two-factor scheme: (1) determining the location of the keyframe with respect to the activation event; and (2) applying a windowed sample selecting rule referred to as "padding." In some embodiments, two types of padding are used. In the first type of padding, any given windowed sample whose keyframe is located inside an activation event is considered as a part of the activation event and therefore included in the training dataset and the model training process. We refer to the first type of padding as the "clamp padding." In the second type of padding, only those windowed samples which are fully inside an activation event are considered as a part of the activation event and therefore included in the training dataset and the model training process. In other words, any partial activation sample is excluded from training dataset and the training process, regardless of the location of the corresponding keyframe. We refer to the second type of padding as the "valid padding." As a result, "padding" scheme determines the type of framework of representing an activation event in the model building process, and can be considered a hyperparameter of the activation detection model.

For example, assuming the center keyframe is used to acquire the label for a windowed sample, and the clamp padding scheme is selected, then a combined "center+ clamp" scheme is selected to include/exclude windowed samples and to represent an activation event in the model building process. Specifically, in the combined "center+ clamp" scheme, those windowed samples, including any partial activation samples whose center keyframes are located inside the activation event are considered as a part of the activation event and therefore included in the training dataset and the model training process. For the exemplary scenario of FIG. 4, selecting the combined center+clamp scheme means that windowed samples 410, 412 and 420 are included to represent activation event 404, wherein the three samples are assigned ground truth labels, 1.0, 1.0, and 0.7, respectively. However, partial activation sample 418 is excluded from representing activation event 404 and from the model training process.

In contrast, assuming the center keyframe is again used to acquire the label but the valid padding scheme is selected instead of the clamp padding scheme, then a combined "center+valid" scheme is selected to include/exclude windowed samples and to represent an activation event in the model building process. Specifically, in the combined "center+valid" scheme, only those windowed samples which are fully inside an activation event are considered as a part of the activation event and therefore included in the training dataset and the training process. In other words, any partial activation sample is excluded from the training dataset and model training, regardless of the location of the corresponding center keyframe. For the exemplary scenario of FIG. 4, selecting the center-valid scheme means that only windowed samples 410 and 412 are included to represent activation event 404, while partial activation samples 418 and 420 are both excluded from representing activation event 404 and from the model training process. It can be readily appreciated that the valid padding scheme will most likely miss the two boundaries of each activation event, whereas the clamp padding scheme will most likely retain the two boundaries of each activation event. As will be discussed below, there can be other keyframe schemes different from the center keyframe scheme. This means there can be other (keyframe scheme+padding scheme) combinations to represent an activation event which differ from the center+clamp or center+valid combined schemes when the center keyframe scheme is replaced with other types of keyframe schemes.

Hyperparameters of the Activation Detection Model

1. Window Length (L)

Note that in the exemplary video sampling process depicted in FIG. 4, the selected window length L is smaller than activation event 404. However, studies of actual activation events from various surgical procedures showed that the durations of individual activation events have a distribution, which means that some activation events can have very short durations while some other activation events can have unusually long durations. Generally speaking, a longer sampling window will contain more video frames and hence more surgical information. As a result, using longer sampling windows to sample a surgical video can generally increase prediction accuracy by reducing false positives (FPs). However, longer sampling windows tend to be less sensitive to those activation events with shorter durations, specifically when the activation durations become shorter than the window length, which can cause false negatives (FNs). This means that shorter windows will have better performance on those short duration activation events. However, shorter sampling windows can also make the model overly sensitive to surgical information, such as energy tool movements, therefore can increase the probability of generating FPs.

In some embodiments, to determine a proper length L for the sampling window, the durations of a large number of actual activation events (e.g., >10,000) are statistically studied, including generating/plotting the statistical distribution of these durations. Next, a window length L can be extracted from the activation duration statistics, such that a predetermined "majority percentage" (e.g., 80%) of the activations have longer durations than the selected window length L.

Figure 5:
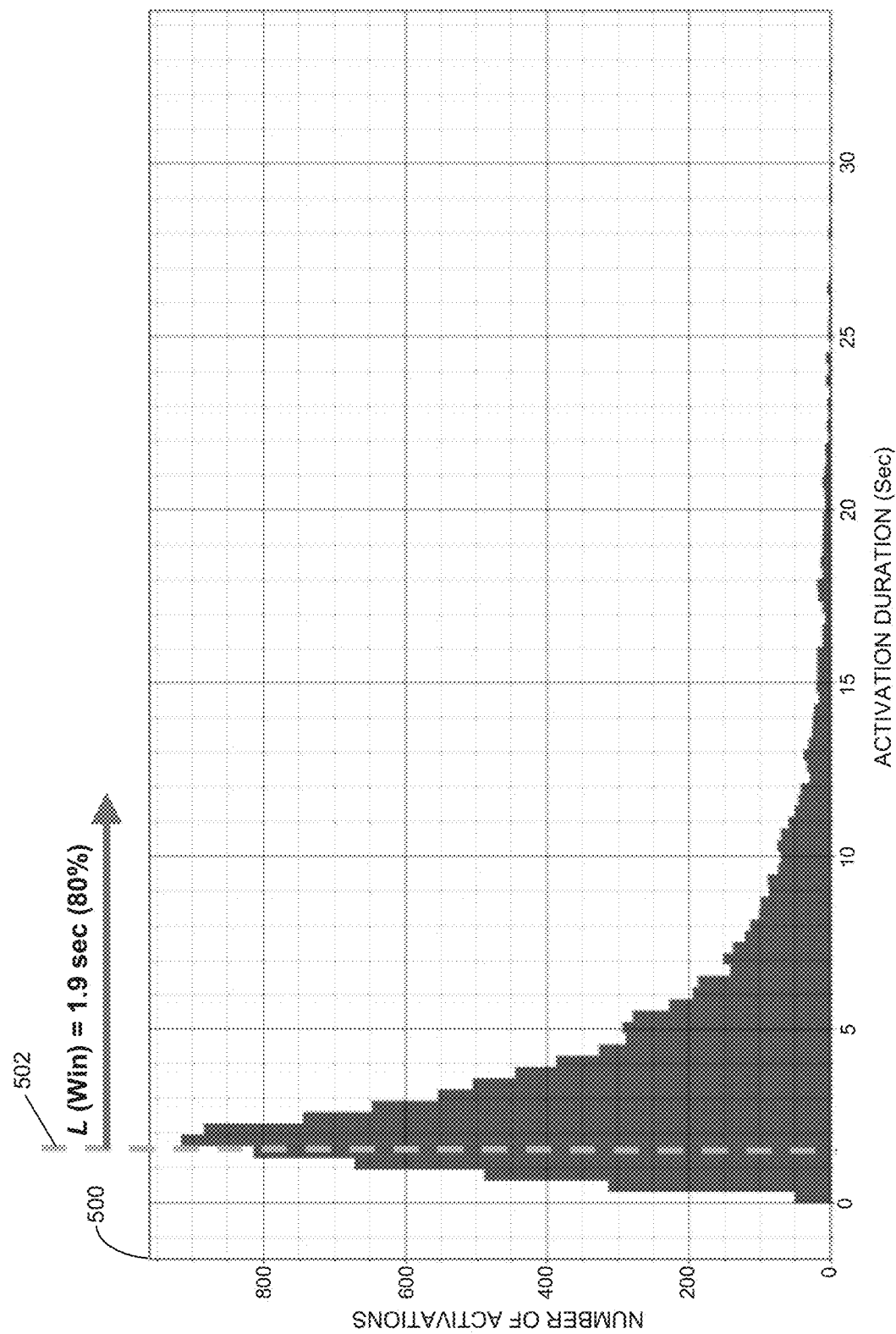
FIG. 5 shows a "number of activations" vs. "activation duration" plot generated based on over 11,000 activations in accordance with some embodiments described herein.

For example, FIG. 5 shows a "number of activations" vs. "activation duration" plot 500 generated based on over 11,000 activation events in accordance with some embodiments described herein. For a predetermined majority of 80%, we can select a window length L such that ~80% of the 11,000 activations have durations longer than this selected window length L. Based on plot 500, a window length of 1.9 sec was selected because ~80% of the 11,000 activations in plot 500 have activation durations longer than 1.9 sec, which can be computed based on the ratio of the two grey areas under plot 500 on either side of the 1.9 sec dividing line 502. Note that in the above exemplary statistics, if the predetermined majority percentage is chosen to be greater than 80%, e.g., 85%, the selected window length L will become shorter than 1.9 sec. Comparing with L=1.9 sec, such a shorter window length will be able to reduce FNs in the remaining 20% of the activation events, but at the cost of increasing FPs. Note that the remaining 20% of the activations with durations shorter than the selected window length L of 1.9 sec can still be included in the training/validation/test datasets, but they can be more challenging for the model because they can be interpreted by the model as partial activations. We will provide the trained activation detection model performance results below for testing different window lengths in combination with other hyperparameters of the activation detection model.

2. Keyframe and Padding

As mentioned above, the keyframe scheme and the padding scheme are two hyperparameters for the activation detection model, and the combined choice of the keyframe scheme and the padding scheme forms the combined "keyframe+padding" scheme (or simply the "keyframe+padding scheme") to represent a given annotated activation event in the training dataset for model training and validation. When describing the concept of keyframe and padding in conjunction with FIG. 4, the center+clamp scheme and the center+valid scheme were described. However, there are a number of other combinations of keyframe+padding schemes and each unique combination can have different impact on the trained activation detection model. Specifically, the center keyframe choice can be replaced with either the "left keyframe" or the "right keyframe" choice, and each of these two new types of keyframe choices can be combined with each of the above-described padding schemes.

Figure 6:
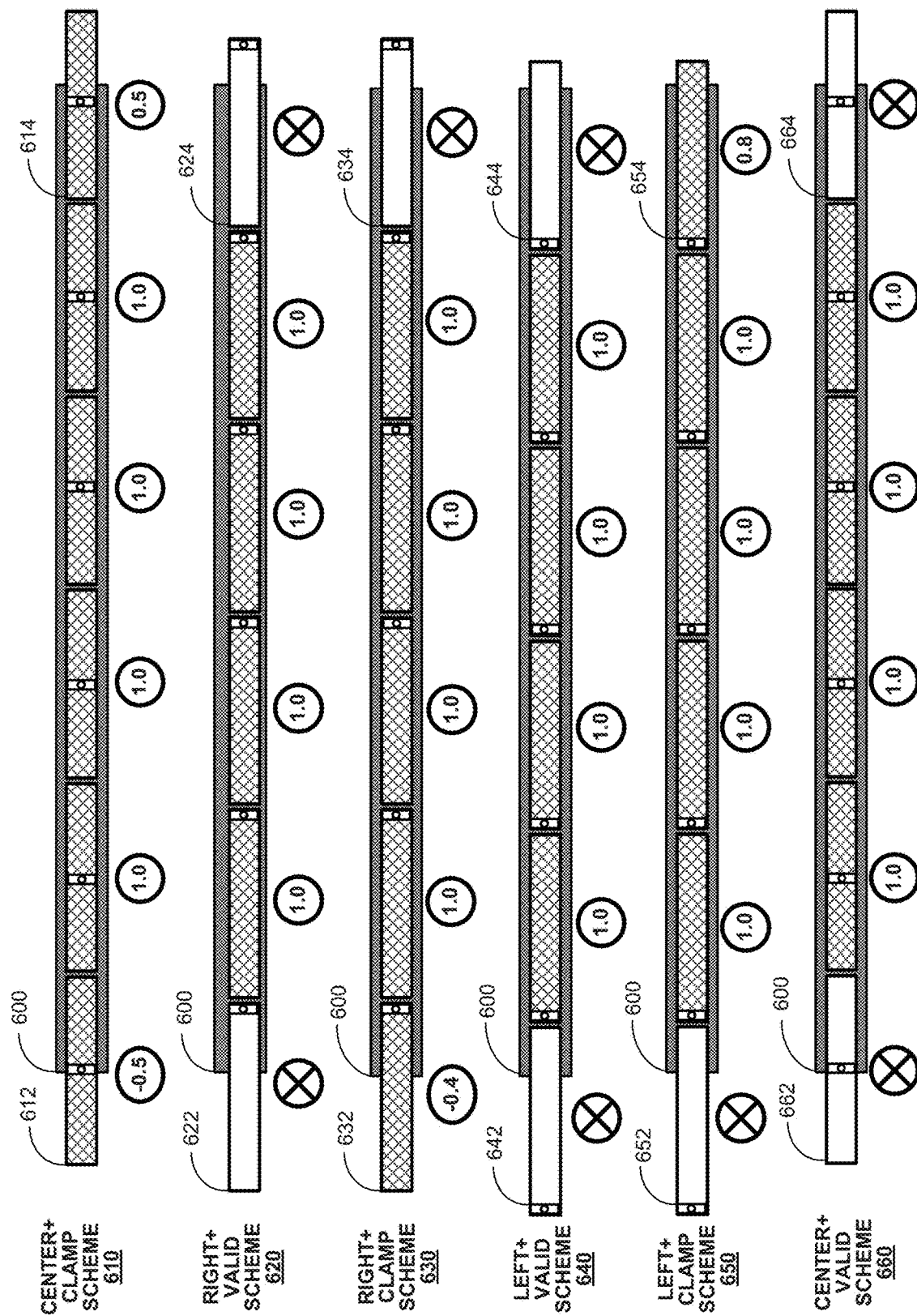
FIG. 6 illustrates various types of combined keyframe+ padding schemes and their respective coverage for the same activation event in accordance with some embodiments described herein.

FIG. 6 illustrates various types of combined keyframe+padding schemes and their respective coverage for the same activation event 600 in accordance with some embodiments described herein. Note that activation event 600 is represented with a dark-shaded window in the background of each illustrated keyframe+padding scheme. As can be seen, a center+clamp scheme 610, which has been discussed above, includes both partial activation samples 612 and 614 to represent activation event 600 during the model training process. This is indicated by a sequence of cross-hatched windowed samples that provides a full coverage for the activation event 600, starting from the partial activation sample 612 on the left and terminating with the partial activation sample 614 on the right. The ground truth labels assigned to these samples are shown underneath the respective samples. Note that to compensate for the partial overlap nature of the partial activation samples 612 and 614, float number −0.5 and 0.5 are assigned to these two samples, respectively, wherein the different signs are used to distinguish their positions on either end of activation event 600. In comparison, the last row in the FIG. 6 shows a center+valid scheme 660, wherein the "valid" padding scheme is selected. As a result, both partial activation samples 662 and 664 are excluded from representing activation event 600 during the model training process, even though the center keyframes of partial activation samples 662 and 664 are both inside the activation event 600. As such, center+valid scheme 660 will miss the coverage for both the beginning (i.e., the close jaws action) and the end (i.e., the open jaws action) of the activation event 600. The ground truth labels 1.0 assigned to the included windowed samples are shown underneath these samples. However, "X" labels are shown underneath partial activation samples 662 and 664 to indicate that these samples are excluded from the training dataset and the model training process in the center+valid scheme.

Next, in a right+valid scheme, such as right+valid scheme 620, the last/end video frame of the windowed sample is selected as the keyframe for each windowed sample. Because "valid" padding scheme is also selected, both partial activation samples 622 and 624 are excluded from representing activation event 600, even when the right keyframe of sample 622 is inside the activation event 600. The ground truth labels 1.0 assigned to the included windowed samples are shown underneath these samples, while "X" labels are shown underneath partial activation samples 622 and 624 to indicate their exclusion from the training dataset and the model training process. Similar to center+valid scheme 660, right+valid scheme 620 will miss the coverage for both the beginning (i.e., the close jaws action) and the end (i.e., the open jaws action) of the activation event 600. In comparison, in a right+clamp scheme, such as right+clamp scheme 630, the "clamp" padding scheme is selected. As a result, the first partial activation sample 632 is included to represent the activation event 600 because the right keyframe of partial activation sample 632 is inside the activation event 600, while the second partial activation sample 634 remains excluded from representing the activation event 600 because the right keyframe of sample 634 is outside of the activation event 600. The ground truth labels assigned to the included windowed samples are shown underneath these samples, which include a float number −0.4 assigned to partial activation sample 632 to compensate for the partial overlap. Note that an "X" label is shown underneath partial activation sample 634 to indicate its exclusion from the training dataset and the model training process. Hence, right+clamp scheme 630 will have the coverage for the beginning (i.e., the close jaws action) of the activation event 600 but will miss the end (i.e., the open jaws action) of the activation event 600.

Next, in a left+valid scheme, such as left+valid scheme 640, the first/leading video frame of the windowed sample is selected as the keyframe for each windowed sample. Because "valid" padding scheme is also selected, both partial activation samples 642 and 644 are excluded from representing activation event 600, even when the left keyframe of sample 644 is inside the activation event 600. The ground truth labels 1.0 assigned to the included windowed samples are shown underneath these samples, while "X" labels are shown underneath partial activation samples 642 and 644 to indicate their exclusion from the training dataset and the model training process. Similar to right+valid scheme 630 and center-valid scheme 660, left+valid scheme 640 will miss the coverage for both the beginning (i.e., the close jaws action) and the end (i.e., the open jaws action) of the activation event 600. In comparison, in a left+clamp scheme, such as left+clamp scheme 650, the "clamp" padding scheme is selected. As a result, the second partial activation sample 654 is included to represent the activation event 600 because the left keyframe of partial activation sample 654 is inside the activation event 600, while the first partial activation sample 652 remains excluded from representing the activation event 600 because the left keyframe of sample 652 is outside of the activation event 600. The ground truth labels assigned to the included windowed samples are shown underneath these samples, which include a float number 0.8 assigned to partial activation sample 654 to compensate for the partial overlap. Note that an "X" label is shown underneath partial activation sample 652 to indicate its exclusion from the training dataset and model training process. Hence, left+clamp scheme 650 will have the coverage for the end (i.e., the open jaws action) of the activation event 600 but will miss the beginning (i.e., the close jaws action) of the activation event 600.

While visually it is reasonable to assume that the center+clamp scheme 610 provides the best overall coverage for the activation events, therefore should be the best modeling choice over other keyframe+padding schemes, it is necessary to test various combined keyframe+padding schemes through a comprehensive model building process to verify the above observations. We will provide the trained model performance results below for testing various keyframe+padding schemes in combination with other hyperparameters of the activation detection model.

3. Stride Between Windows

Figure 7:
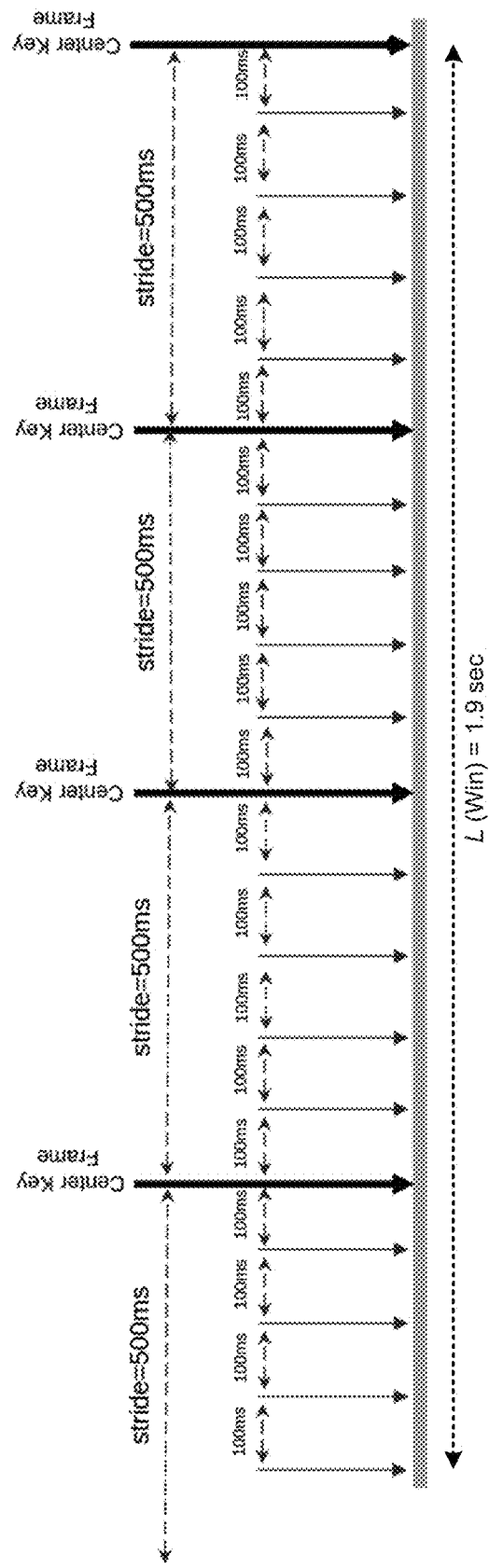
FIG. 7 shows an exemplary windowed sampling scheme that includes an overlap between adjacent samples/clips for the selected window length (i.e., 1.9 seconds) in accordance with some embodiments described herein.

In the window-based video sampling schemes described above, we have assumed that the windows are sequentially applied end-to-end without overlap or spacing between two consecutive/adjacent windowed samples. In other words, the stride that equals the window length is used in these examples. However, in other embodiments of sampling an annotated surgical video, the stride can be made a variable/hyperparameter to test different amounts of overlaps between adjacent samples/clips. Specifically, when the stride is made to be smaller than the window length, the windowed samples become overlapped. This means that the same video frame can be included in multiple (i.e., 2 or more) consecutive window samples/clips, thereby increasing the resolution of the disclosed window-based video segmentation and processing. Note that using overlapping windows also creates more opportunities for data augmentation. Note also that by including the overlap between adjacent windows, the distance between adjacent keyframes is also reduced. FIG. 7 shows an exemplary windowed sampling scheme 700 that includes an overlap between adjacent samples/clips for the selected window length (i.e., 1.9 seconds) in accordance with some embodiments described herein. As can be seen in FIG. 7, a stride of 0.5 seconds is used between adjacent windows (which is the same distance between adjacent keyframes) to create 1.4 seconds of overlap between any two adjacent windows. However, other embodiments of the disclosed activation model can use other window lengths greater or shorter than 1.9 seconds, and/or strides between windows greater or shorter than 0.5 seconds.

Figure 8:
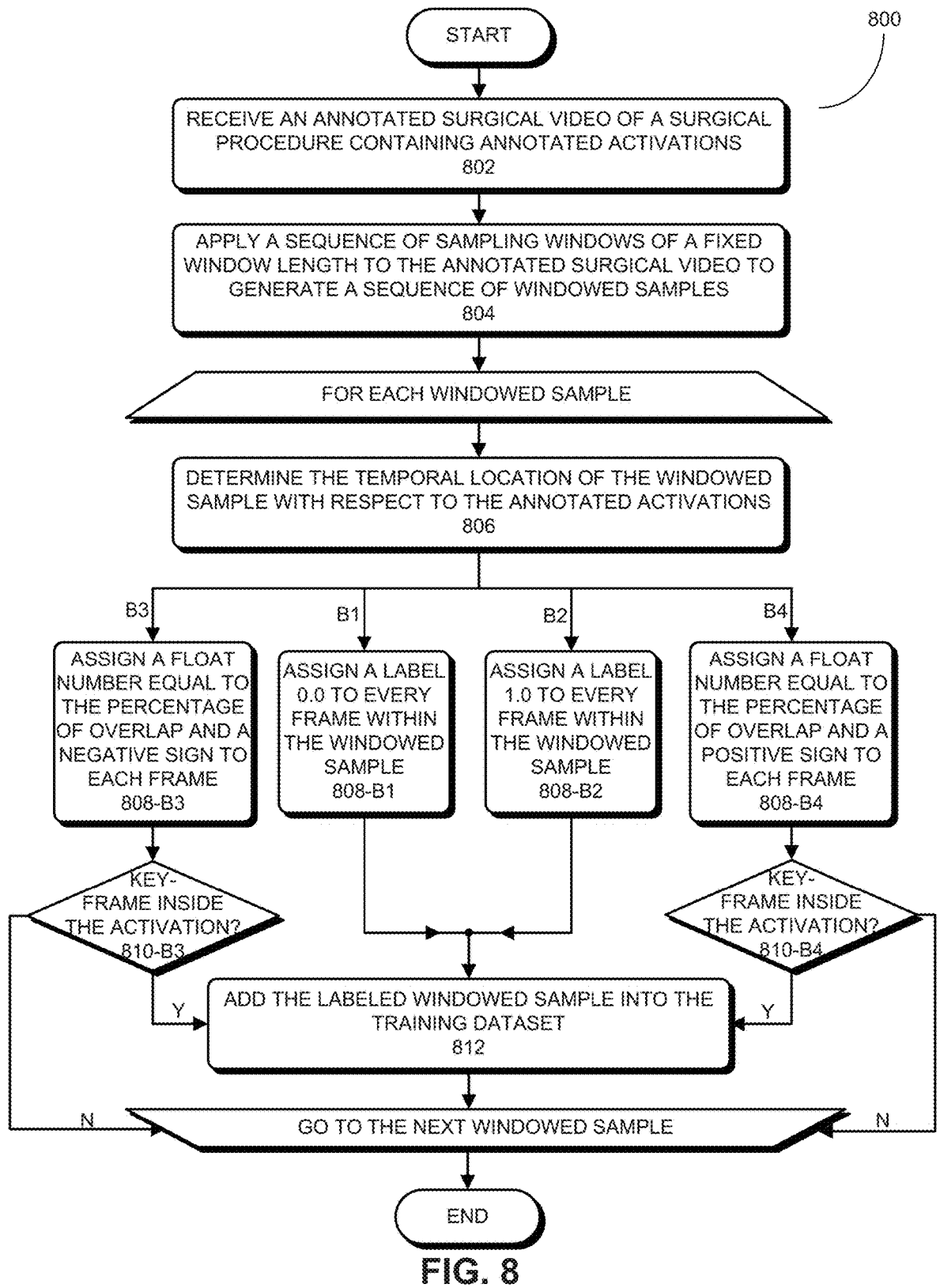
FIG. 8 presents a flowchart illustrating a process for generating a training dataset for the activation detection model from an annotated surgical video containing annotated activation events in accordance with some embodiments described herein.

FIG. 8 presents a flowchart illustrating a process for generating a training dataset for the activation detection model from an annotated surgical video containing annotated activation events in accordance with some embodiments described herein. In one or more embodiments, one or more of the steps in FIG. 8 may be omitted, repeated, and/or performed in a different order. Accordingly, the specific arrangement of steps shown in FIG. 8 should not be construed as limiting the scope of the technique.

Process 800 may begin by receiving an annotated surgical video of a surgical procedure containing annotated activation events (step 802). In some embodiments, the annotated surgical video was generated from a raw surgical video using the processes and techniques disclosed in conjunction with FIGS. 2-3. Process 800 next applies a sequence of sampling windows of a predetermined window length to the annotated surgical video to generate a sequence of video clips/samples of the annotated surgical video (step 804). In some embodiments, the predetermined window length is determined based on a statistical study of the durations of the activation events associated with the surgical procedure, such that a predetermined majority percentage (e.g., 80%) of the activation events have longer durations than the selected window length. In some embodiments, the sequence of sampling windows includes a predetermined stride between adjacent windows, wherein the stride can have a value between a given percentage of the window length (e.g., 20%) to the full window length. Note that when the predetermined stride is equal to the full window length, there is no overlap between adjacent windows. However, when the predetermined stride is smaller than the full window length, there is an amount of overlap between adjacent windows, wherein the amount of overlap increases with decreasing stride size.

Next, for each windowed sample/video clip in the sequence of windowed samples, process 800 determines the temporal location of the windowed sample with respect to the annotated activation events in the annotated surgical video (step 806). In various embodiments, process 800 can determine the temporal location of the windowed sample relative to the activation events based on (1) the first/leading frame of the windowed sample, or (2) the last/end frame of the windowed sample, or (3) the center frame of the windowed sample, or (4) a combination of the above three frames. After determining the temporal location of the windowed sample, process 800 may split into fourth branches:

1st Branch (B1): when the windowed sample is determined to be fully inside a non-activation period, e.g., sample 414 in FIG. 4;

2nd Branch (B2): when the windowed sample is determined to be fully inside an annotated activation event, e.g., sample 412 in FIG. 4;

3rd Branch (B3): when the windowed sample is determined to partially overlap with the leading portion of an annotated activation event, e.g., sample 612 in FIG. 6; and 4th Branch (B4): when the windowed sample is determined to partially overlap with the ending portion of an annotated activation event, e.g., sample 614 in FIG. 6.

Specifically, in the first branch, process 800 assigns a ground truth label 0.0 to each frame within the windowed sample (step 808—B1). The labeled windowed sample is then added into the training dataset (step 812), and process 800 returns to process the next windowed sample. In the second branch, process 800 assigns a ground truth label 1.0 to each frame within the windowed sample (step 808—B2). The labeled windowed sample is then added into the training dataset (step 812), and process 800 returns to process the next windowed sample.

In the third branch, process 800 assigns a float number between 0.0 and 1.0 with a negative sign and a value equal to the percentage of overlap with the activation event to each frame within the windowed sample (step 808—B3). Process 800 additionally determines if a selected keyframe, e.g., the center keyframe of the windowed sample is also inside the given activation event (step 810—B3). If so, the labeled windowed sample is added into the training dataset (step 812), and process 800 returns to step 806 to process the next windowed sample. Otherwise, the labeled windowed sample is excluded from the training dataset, and process 800 directly returns to process the next windowed sample. In some embodiments, the step 810—B3 can be omitted and process 800 goes directly to step 812 to add the labeled windowed sample into the training dataset.

In the fourth branch, process 800 assigns a float number between 0.0 and 1.0 with a positive sign and a value equal to the percentage of overlap with the activation event to each frame within the windowed sample (step 808—B4). Process 800 additionally determines if a selected keyframe, e.g., the center keyframe of the windowed sample is also inside the given activation event (step 810—B4). If so, the labeled windowed sample is added into the training dataset (step 812), and process 800 returns to process the next windowed sample. Otherwise, the labeled windowed sample is excluded from the training dataset, and process 800 directly returns to process the next windowed sample. In some embodiments, the step 810—B4 can be omitted and process 800 goes directly to step 812 to add the labeled windowed sample into the training dataset.

As a variation to step 804, the sequence of sampling windows in step 804 can be replaced with a single sampling window so that the sampling windows are applied to the annotated surgical video one at a time. Next, the sequence of steps 806-812 is applied to the single sampling window. Hence to process the annotated surgical video, the modified process 800 will loop over the sequence of steps 804-812 for a sequence of applied sampling windows.

Construction of and Using Training Dataset for Model Training and Validation

In a particular implementation of the disclosed training dataset construction procedure, 183 surgical videos are included, which comprise 57 gastric bypass procedural videos and 126 sleeve gastrectomy procedural videos. After applying the disclosed surgical video annotation procedure described in conjunction with FIGS. 2-3, by four (4) independent and trained annotators, a total of 11302 activations are identified and annotated, which amount to 48387 seconds of activation. The annotated videos are then split into 75% for model training, 15% for model validation, and 10% for model testing. After applying the disclosed window-based sampling and labeling procedure described in conjunction with FIGS. 4-8 to different groups of the annotated surgical videos, 117,032 windowed samples/video clips are generated, of which 95249 samples are used as training samples and 21783 samples are used as validation samples. Furthermore, among the 95249 training samples, 40035 are positive samples (i.e., samples labeled as activation), while 55214 are negative samples (i.e., samples labeled as no activation).

In some embodiments, to address skewness in the training dataset between the positive samples and negative samples, the "negative log likelihood" loss function with penalties proportional to the total number of each type of labeled samples are used to reduce or eliminate bias to either type of label in the classification outputs of the trained model. Another approach to mitigate the skew in the training dataset is to sort the training samples in the training dataset based on the associated amount of loss in the cost function and choose those training samples that have higher loss values. In other words, we only keep those more difficult samples that are causing larger amount of losses in the cost function. Yet another approach to mitigate the skew in the training dataset is to assign weights on each training sample in each epoch of training based on the loss value associated with that sample, and reduce the chance of selecting those training samples that have lower cost during the next epoch of training.

In some embodiments, an overall 12 activation detection models with different combinations of the described hyper-parameters (i.e., by using different keyframe locations, the padding types, the window lengths, and the strides, among others) are set up and then trained over a number of N epochs (e.g., N=200) based on the training dataset and validation dataset constructed using the above-described techniques. This allows a particular model among the 12 trained activation detection models that provides the best overall performance to be identified. More detail in the model comparisons and optimal model identification is provided below.

In some embodiments, in each epoch of the model training process, a different data augmentation set composed of a randomly-selected set of image-transformation functions is applied to the originally labeled training dataset (or "the original training dataset") to increase the diversity and size of the training dataset. Note that augmenting the original training data allows more real-world scenarios of surgical video images that might not be included in the original training dataset to be artificially generated and covered. Generally speaking, the data augmentations to the original training dataset are applied on the video-clip basis, meaning that a given image-transformation function, once selected for a labeled sample in the training dataset, is applied to the entire labeled sample (i.e., to every frame of the sample).

Note that there can be three levels of randomness in applying an image-transformation function to a given labeled training sample: (1) a randomness in terms of the type of image transformation (e.g., by randomly applying one of many types of affine transformations to the training sample); (2) a randomness in terms of transformation parameters used in the randomly-applied transformation type (e.g., a random amount of rotation, a random axis of flipping, a random angle of shearing, or a random percentage of zooming for a given type of affine transformation); and (3) a randomness in applying or not applying an applied transformation. Note that the randomness in applying the image-transformation function to each labeled training sample makes each data augmentation set for each epoch of model training unique from other epochs. In some embodiments, in each epoch of the model training process, the data augmentations are only applied to one portion of the training dataset, while the other portion of the training dataset is unaltered. For example, the data augmentations may be applied to 50% of the training dataset in each epoch of training, while the other 50% of the training dataset is not augmented in the epoch of training. Moreover, the ratio of augmented training samples to non-augmented training samples can be different in different epochs of training. A person skilled in the art would appreciate that after a given data augmentation technique is applied to a labeled sample within the training dataset, the label of the augmented sample is not changed.

Note that the data augmentation techniques that can be used on the training dataset can include various geometrical transformations, such as image rotation, image flipping, image shearing, image zooming, and image padding. The data augmentation techniques can also include various color, brightness, and contrast manipulations. Moreover, the data augmentation techniques can also include temporal-based transformations. For example, one proposed temporal based transformation can randomly reverse the timestamps of a given video clip/windowed sample and plays the temporally-transformed clip/sample backward. We denote the transformation function that performs the disclosed random temporal transformation as "RandomTemporalFlip." Note that the "Randomness" in the proposed RandomTemporalFlip function means that after the function is applied to a training sample, the timestamps in the training sample may or may not be reversed. In one particular embodiment, a data augmentation set applied to a particular training epoch is composed of the following set of transformations: SquarePad, Resize, Normalization, RandomHorizontalFlip, RandomColorJitter, RandomAffine, and RandomTemporalFlip. Regardless the transformation function applied on an original training sample, the resulting augmented sample should have the same activation/non-activation label as the original training sample.

Using Trained Activation Detection Model for Surgical Video Inferences

Figure 9:
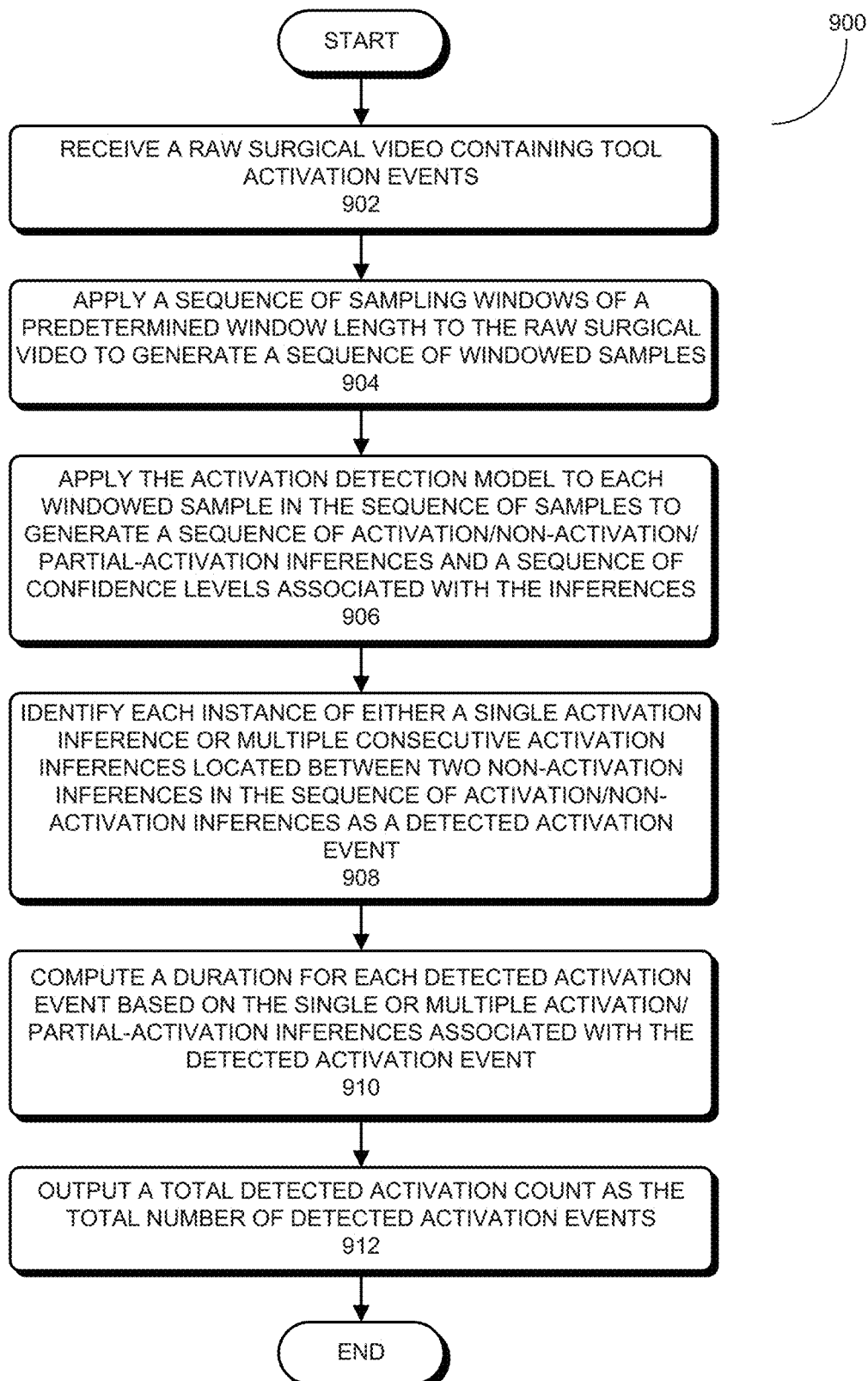
FIG. 9 presents a flowchart illustrating a process for using the disclosed activation detection model on a raw surgical video to automatically infer activation events in the raw surgical video in accordance with some embodiments described herein.

FIG. 9 presents a flowchart illustrating a process for using the disclosed activation detection model on a raw surgical video to automatically infer activation events in the raw surgical video in accordance with some embodiments described herein. In one or more embodiments, one or more of the steps in FIG. 9 may be omitted, repeated, and/or performed in a different order. Accordingly, the specific arrangement of steps shown in FIG. 9 should not be construed as limiting the scope of the technique. In process 900, it is assumed that the disclosed activation detection model has been sufficiently trained or both trained and validated.

Process 900 may begin by receiving a raw surgical video, such as a raw endoscope video of the surgical procedure containing energy-tool activation events (step 902). Process 900 next applies a sequence of sampling windows of a predetermined window length to the raw surgical video to generate a sequence of video clips/samples of the raw surgical video (step 904). In some embodiments, the predetermined window length used for video inference in process 900 is identical to the above-described predetermined window length used for constructing the training dataset. In some embodiments, the sequence of sampling windows applied to the raw surgical video includes a stride between adjacent windows, wherein the window stride can have a value between a given percentage of the window length (e.g., 20%) to the full window length. Note that the window stride used in process 900 to sample the raw surgical video for video inference can be different from the above-described window stride used to sample the annotated surgical video for constructing the training dataset. For example, the window stride for video inference can be selected to be equal to the predetermined window length so that the sequence of sampling windows is applied to the raw surgical video end-to-end without overlap between adjacent windows, while the window stride used for activation model construction can be less than the predetermined window length. As another example, the window stride for process 900 can be selected to effectuate an amount of overlap between adjacent sampling windows, but the selected window stride can be different from the window stride used for constructing the activation model.

Next, the disclosed activation detection model is applied to each windowed sample in the sequence of windowed samples to generate an activation/non-activation/partial-activation inference (step 906). Specifically, the disclosed activation detection model processes each windowed sample by applying the activation detection model to the sequence of video frames within the windowed sample and predicting whether the windowed sample is (1) fully inside a non-activation period (i.e., making a "non-activation" or "0" inference), or (2) fully inside an activation event (i.e., making an "activation" or "1" inference), or (3) partially overlapping with an activation event (i.e., making a "partial activation" inference using a float number that is between −1 and 1). Note that for each partial-activation inference, the associated float number generated by the model carries two pieces of information: (1) the sign of the float number indicates whether the predicted partial activation sample is at the beginning or the end of the detected activation event, e.g., "negative" means the partial overlap is with the beginning of the activation, and "positive" means the partial overlap is with the end of activation, and (2) the fractional value of the float number represents the amount of the overlap (e.g., in terms of the percentage of the window length) with the detected activation event. As a result, the disclosed activation detection model outputs a sequence of activation/non-activation/partial-activation inferences for the sequence of windowed samples.

Next, process 900 identifies each instance of either a single activation/partial-activation inference or multiple consecutive activation/partial-activation inferences located between two non-activation inferences in the sequence of activation/non-activation/partial-activation inferences as a detected activation event (step 908). It can be readily appreciated that the first and the last inferences in the multiple consecutive activation/partial-activation inferences are the two partial-activation inferences having the signed float numbers. Moreover, the signs of the float numbers can be used to distinguish the two partial-activation inferences. Process 900 next computes a duration for each detected activation event based on the single or multiple consecutive activation/partial-activation inferences associated with the detected activation event (step 910). Process 900 can additionally outputs a total detected activation count as the total number of detected activation events (step 912). Note that the total detected activation count can be generated for the entire surgical video or for a portion of the surgical video corresponding to a specific surgical task/step.

In some embodiments, for each detected activation event composed of multiple consecutive activation/partial-activation inferences, process 900 can compute the duration of the detected activation event as follows: (1) computing a first partial activation duration for the first partial-activation inference in the multiple consecutive inferences by multiplying the window length with the non-sign float number associated with the first partial-activation inference; (2) computing a second partial activation duration for the second partial-activation inference in the multiple consecutive inferences by multiplying the window length with the non-sign float number associated with the second partial-activation inference; (3) computing a third partial activation duration by multiplying the window length with the number of activation inferences between the first partial-activation inference and the second partial-activation inference (assuming that there are at least 3 consecutive activation/partial-activation inferences); and (4) summing up the first, the second, and the third partial activation durations to obtain the activation duration for the detected activation event. Clearly, if there are only two partial-activation inferences for the detected activation event, the third partial activation duration becomes zero and the activation duration is the sum of the first and the second partial activation durations. In some embodiments, if a detected activation event contains only a single activation/partial-activation inference, then the activation duration can be computed by multiplying the window length with the confidence level associated with the single partial-activation inference.

As an alternative embodiment to step 906 described above, the disclosed activation detection model can also generate a sequence of activation/non-activation inferences and a sequence of associated confidence levels for the sequence of windowed samples. Specifically, the disclosed activation detection model processes each windowed sample to predict whether the windowed sample is inside a non-activation period (i.e., making a "non-activation" inference), or a part of an activation event (i.e., making an "activation" inference). Note that in this embodiment, an activation inference for a windowed sample includes both the scenario of fully-inside an activation event and the scenario of partially-overlapping an activation event. Moreover, the confidence level generated by the activation detection model, which is a fractional number, can be configured to represent the amount of the overlap (e.g., in terms of the percentage of the window length) of a partial activation sample with the detected activation event. Note that there are at most two partial activation samples for each detected activation event, which can be identified as the first and the last activation inferences in multiple consecutive activation inferences for the detected activation event. Once these two partial activation samples are identified, their associated confidence levels can be used to determine the amount of overlaps, which are subsequently used for determining an accurate duration of the detected activation event.

Model Validation Results Discussion

As described above, the disclosed activation detection model can be configured to output predicted durations of the detected activation events. However, the disclosed activation detection model can be easily re-configured to output the number of detected activation events (i.e., a total activation count), because each detected activation event by the activation detection model just increments a total activation count by 1. It can be readily perceived that when the output of the activation detection model is converted from "activation durations" to "activation count," the F1-score of the model predictions will increase because counting the number of detected activation events is inherently a simpler problem than measuring the length of each detected activation event. Generally speaking, if an activation event has been detected for the first time, any false negative (FN) inference generated within the corresponding activation duration will have no negative impact on the activation count simply because that activation has already been counted.

FIG. 16 shows Table 1 which is the summary of model validation results of 12 activation detection models trained with different model parameters and evaluated using the same validation dataset in accordance with some embodiments described herein. As can be seen in Table 1, the model parameters that are varied in the 12 activation detection models include some of the above-described hyperparameters, i.e., (1) the sampling window length (in Column C5); (2) the padding scheme (in Column C4); and (3) the keyframe location (in Column C3). Specifically, for the window length hyperparameter, three window lengths 1.4-sec, 1.6-sec, and 1.9-sec are tested. For the padding schemes, both valid and clamp schemes are tested. For the keyframe location hyperparameter, right and center choices are tested. However, the same stride hyperparameter value is used for all 12 activation detection models. In addition to these hyperparameters, other model parameters that are varied for the 12 activation detection models include: (4) SoftMax threshold value (in Column C7); and (5) data augmentation functions (not listed in Table 1). Note that while only SoftMax thresholds 0.4 and 0.5 are listed in Table 1, it should be noted that other threshold values of SoftMax from 0.1 to 0.9 with the step of 0.1 are also tested, and thresholds 0.4 and 0.5 are found to have better performances.

For model performance evaluation, F1-score (in Column C8) of the model inference outputs on the validation dataset is calculated for each model as a common performance metric. Other computed performance evaluation metrics include: (1) activation-duration-prediction accuracy of each model, which is denoted as "Act_Dur_Acc" and listed in Column C9; and (2) activation-count-prediction accuracy of each model, which is denoted as "Act_Num_Acc" and listed in Column C10. It can be observed from Table 1 that a model with a better F1-score does not necessarily have a better performance in terms of predicting activation durations and counting the number of the detected activation events. For example, if we compare model F2 (i.e., model #2 in Table 1) and G2 (i.e., model #6 in Table 1), we will see that model G2 has a higher F1-score than model F2, but model F2 has better performances than model G2 in both predicting activation durations and counting the number of activations. The same phenomenon can be observed when we compare the performance metrics of model L2 and model F1. This seems to suggest that the traditional F1-score may not be the most meaningful performance metric for the disclosed activation detection model.

In some embodiments, a new performance metric that is closely related to the targeted clinical applications of the activation detection model, denoted as "Act_Acc" is introduced and defined as follows:

$$\text{Act\_Acc} = \frac{2(\text{Act\_Dur\_Acc} \cdot \text{Act\_Num\_Acc})}{\text{Act\_Dur\_Acc} + \text{Act\_Num\_Acc}},$$

wherein performance metrics Act_Dur_Acc and Act_Num_Acc have been defined above. Hence, the new metric Act_Acc is formulated based on both the accuracy of the predicted durations of the detected activation events and the accuracy of the predicted total activation count. Based on the computed values of the Act_Acc metric in Column C11, the best performing model is identified to be model F1 which is listed in row #1 of Table 1.

It can also be observed from Table 1 that, as the window length (in C5) is increased from 1.4-sec to 1.6-sec and 1.9-sec, both activation duration inference accuracies Act_Dur_Acc and activation count inference accuracies Act_Num_Acc are improved. In terms of stride choices, it is observed that if the overlap between two consecutive sampling windows is increased, the estimates of the activation duration tend to become more accurate, while the estimates of the activation count become less accurate. This observation suggests that the stride, and hence the overlap between the applied windows should be judicially selected based on specific use cases.

An additional observation from Table 1 is that in general all 12 models show a higher accuracy in predicting the durations of activations than counting the number of activations. In other words, Act_Dur_Acc values are consistently higher than Act_Num_Acc values across all 12 models. It can be further observed that Act_Dur_Acc values and Act_Num_Acc values have certain correlations as they increase and decrease coherently.

Activation Detection Model Applications

For a given surgery procedure, there can be wide variations in energy device technologies, energy delivery types, and device model choices, even within the same surgical step, which generally depend on surgeon preference or hospital availability. For example, monopolar cautery, bipolar cautery, and ultrasonic devices can all be used for the dissection of lesser sac in a Roux-en-Y gastric bypass procedure. These surgical techniques differ in terms of the microscopic impact on the target tissue, as well as the amount of spread to surrounding tissues. However, there is general lack of understanding whether these differences have clinical significance, such as in relation to surgery efficiency or bleeding, among other patient outcomes. Some known studies in such differences are generally theoretical based.

The disclosed energy tool activation detection models and techniques combined with the energy tool presence/absence detection model and technique disclosed in the co-pending U.S. patent application Ser. No. 17/566,116 (filed on Dec. 30, 2021, the content of which is incorporated by reference herein) can facilitate gathering energy device annotations and statistical data from an ever-growing supply of surgical video recordings. Using the disclosed activation detection models and the presence/absence detection model, the following energy device usage data can be extracted for each energy tool from each recorded surgical video: (1) the duration of on-screen presence of the energy tool; (2) the total number of activations of the energy tool; and (3) the total duration of detected activation events of the energy tool. Note that both the disclosed activation detection model and the presence/absence detection model are applicable to a wide variety of energy devices including at least bipolar and ultrasonic energy devices. After extracting the energy device usage data from the large cache of surgical videos, surgeons can leverage the energy device usage data to establish associations/correlations between the energy device usage data and numerous surgical events and specifications. These surgical events and metrics can include, but are not limited to the following categorizes:

(1) Energy tool types and models: the extracted energy device usage data can be categorized based on the energy delivery types (e.g., monopolar, bipolar, ultrasonic) and/or based on energy tool models (e.g., Harmonic™, LigaSure™, Enseal™ Sonicision™);

(2) Activation Durations: the detected activation events in the extracted energy device usage data can be categorized based on the activation durations, e.g., into the following 5 categories: >0 sec; >5 sec; >10 sec; >15 sec; and >20 sec;

(3) Tool usage modes, including "scoring," "grasping," and "retraction": note that these are energy-tool usage modes that do not involve activations. Categorizing these non-activating use modes is beneficial for tool-use training purposes;

(4) Adverse events, including "bleeding," "burning," and "injury": establishing the correlations between the extracted energy device usage data and the adverse events can help to understand the root causes of these adverse events, and identify inappropriate uses of the energy device that lead to the adverse events. Note that each type of adverse event can bring harm to the patient and add extra time to the surgery while waiting for recovery from the adverse situation. For example, bleeding not only leads to loss of the blood, but adds extra time to the surgery due to the reduced visibility of the operating area;

(5) Jaw/tissue improper-contact types, including "overstuffed jaws," "excessive tissue tension," and "incomplete vessel capture": note that the extracted energy device usage data may help to detect these impropercontacts between the jaws of the energy tool and the tissue before the energy is applied on the tissue. This will allow the jaws of the device to be repositioned for better dissecting and sealing and to avoid the above mentioned adverse effects;

(6) Case complexity levels, including "low," "medium," and "high": note that the extracted energy device usage data can help to establish the relationship between the number of detected activations and the complexity level of a procedure. For example, excessive activations than normal may be an indicator of a higher complexity of a given procedure;

(7) Tissue types, including "fat" and "Nonfat:" establishing the correlations between the extracted energy device usage data and various tissue types can help to develop a program to customize energy delivery (e.g., the total energy dose) based on the target tissue type;

(8) Tissue thickness, such as "thin," "medium," and "thick": note that because tissue thickness plays an important role in determining a desired and safe energy power level, establishing the correlations between the detected activation events and various tissue thicknesses can help to develop a program that automatically stops the activation in accordance with the target tissue thickness;

(9) Sealing qualities, including "low," "acceptable," and "ideal": note that associating the extracted energy device usage data with resulting sealing qualities may allow sealing quality to be inferred based on the energy device usage data, and help create a library of different sealing quality classifications (e.g., "bad" sealing cases vs. "good" sealing cases) for training purposes;

(10) Jaw bite types, including "full" and "partial": note that it is possible to establish correlations between the bite types and the sealing quality without using energy device usage data;

(11) Tissue appearances after being subjected to activations, including "charred," "wet," and "sticking" etc.: that note establishing the correlations between the extracted energy device usage data and post-activation tissue appearances can help to prevent these undesirable situations and guide clean and effective activations on any given tissue;

(12) Surgical tasks and steps: the extracted energy device usage data can be used to establish a standard in what nominal energy dosage to be applied to a particular surgical task/step, which can then be used for training new surgeons; and

(13) Patient outcome types: it is useful to establish correlations between patient recovery speed and the sealing qualities mentioned above, which themselves are associated with the extracted energy device usage data.

Activation Detection Model Use Case #1

Figure 10:
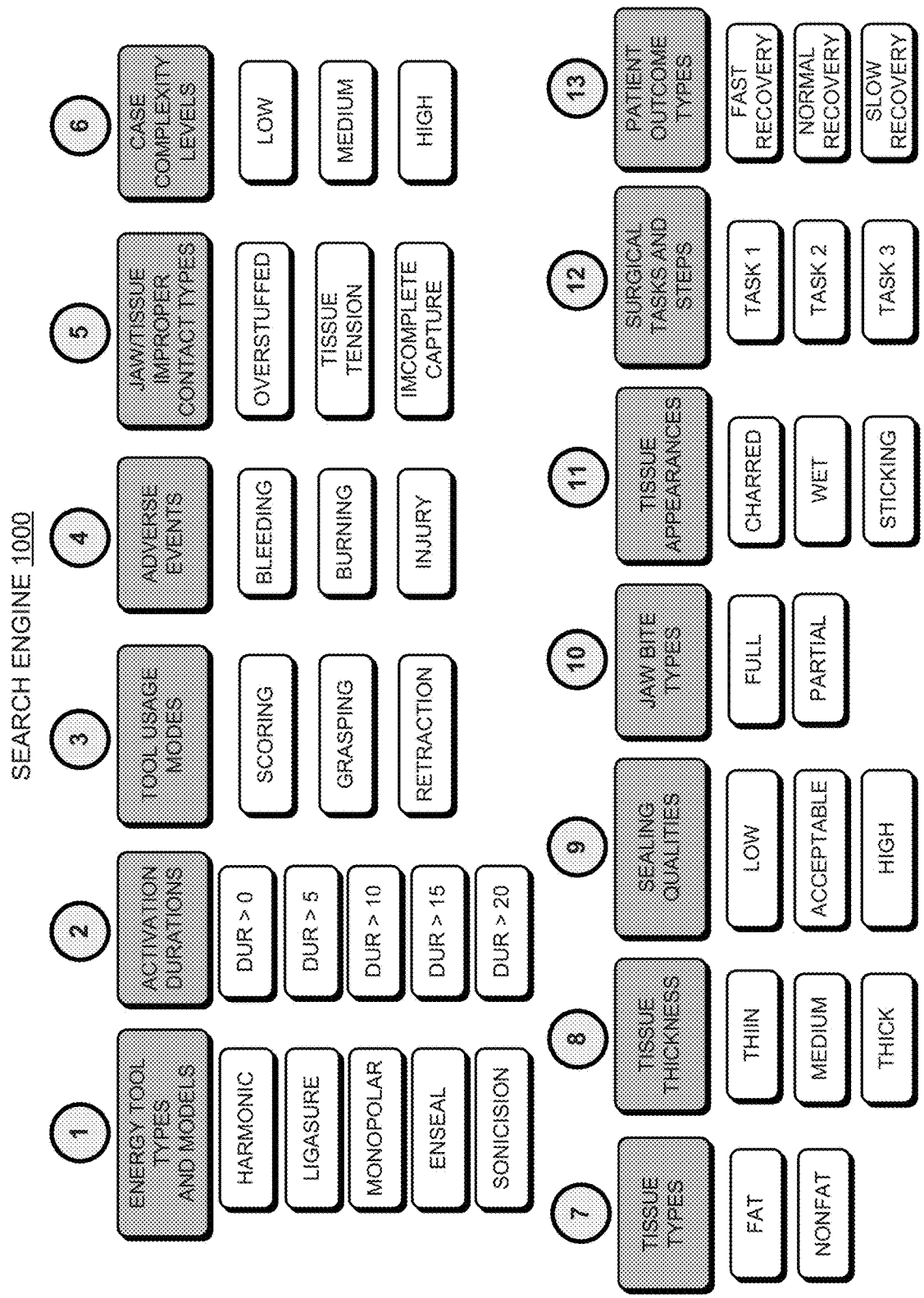
FIG. 10 shows the design of a search engine that includes 13 categories of energy-tool-usage-related events and metrics for querying any of these events and metrics based on a user's request in accordance with some embodiments described herein.

After establishing the above categories of surgical events and metrics based on the extracted energy device usage data, a search engine can be constructed to facilitate searches of each of the above categories and the associated subcategories. FIG. 10 shows the design of a search engine 1000 that includes 13 categories of energy-tool-usage-related events and metrics for querying any of these events and metrics based on a user's request in accordance with some embodiments described herein. In some embodiments, a user selects a given category among the 13 categories shown in search engine 1000 and/or an associated subcategory of the selected main category. In response, search engine 1000 will return the list of activations that matches the requested category and/or the associated subcategory, which can be extremely useful for both research and education purposes.

Activation Detection Model Use Case #2

Figure 11:
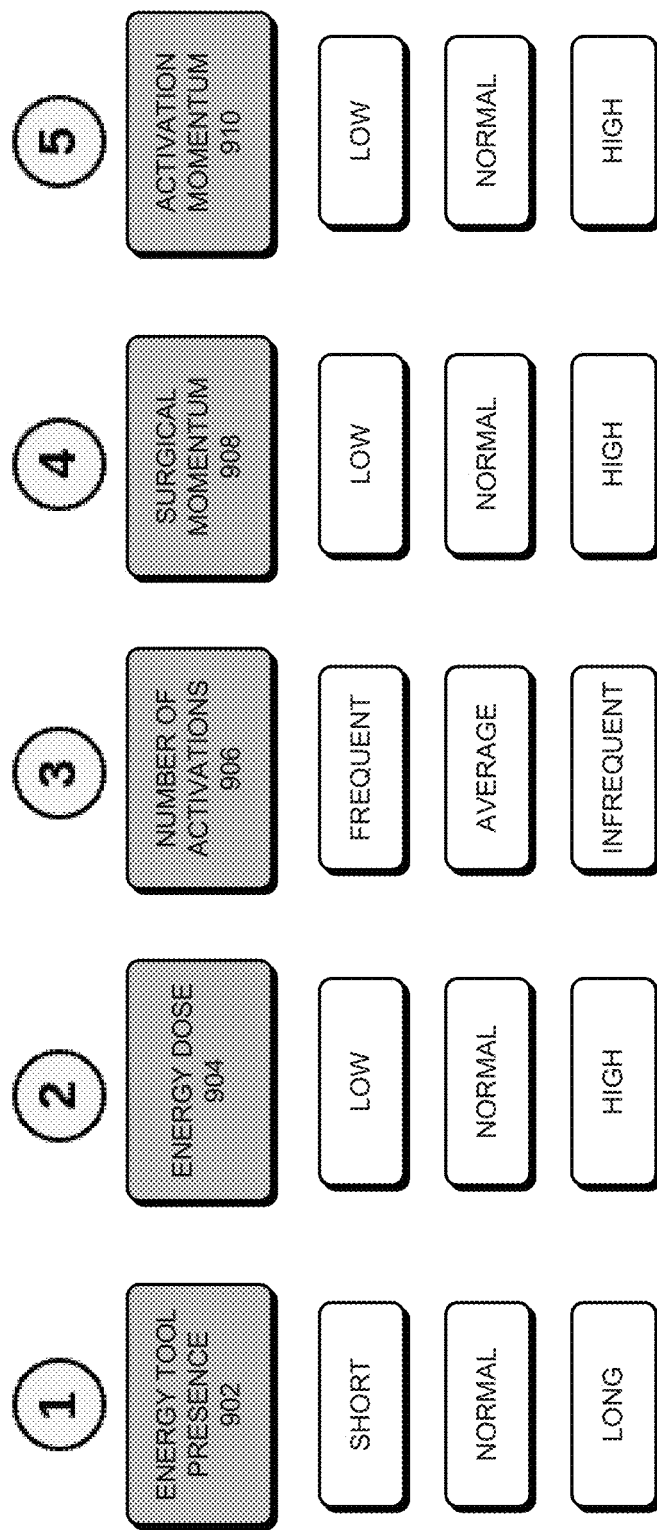
FIG. 11 shows the design of a search engine that can be used for evaluating a particular surgical procedure performed by a particular surgeon in accordance with some embodiments described herein.

FIG. 11 shows the design of a search engine 1100 that can be used for evaluating a particular surgical procedure performed by a particular surgeon in accordance with some embodiments described herein. To construct search engine 1100, the energy tool usage data including activation data (i.e., number of activations and activation event durations) from a large number of surgical procedures involving the energy tool are extracted and analyzed. In particular, the analyses of the extracted energy tool usage data include establishing a gold standard of energy tool use, wherein the gold standard further includes defining a set of standards, such as "High" vs. "Low;" "Long" vs. "Short;" "Frequent" vs. "Infrequent," etc.

As can be seen in FIG. 11, search engine 1100 can include the following indexed categories of energy tool use metrics: (1) energy tool presence 1102; (2) energy dose 1104; (3) number of activations 1106; (4) surgical momentum 1108; and (5) activation momentum 1110. Note that because search engine 1100 is constructed based on the data collected from a large number of energy tools associated with a large number of surgical procedures, each of the above categories of energy tool use metrics can reflect a range of variations in how the energy tools are used during in the same surgical procedure and within the same surgical steps. These variations can be correlated to clinically significant differences in outcomes, and provide a framework to further study and identify the optimal techniques of energy tool usage to improve tool use efficiency and patient outcomes. In addition, these categorized activation data can be used to further understand the value of certain techniques given the wide variation in energy device expenses.

Note that search engine 1100 shows two new proposed activation event metrics for quantifying the activation pattern during the surgery: (1) "surgical momentum" and (2) "activation momentum" which are both derived based on the extracted energy tool presence data and the extracted number of activation data. Specifically, the surgical momentum metric can be calculated in terms of the number of activations per unit time (e.g., per minute) of the on-screen presence of the energy tool (i.e., as the ratio of the total activation-event count during a surgery to the combined on-screen presence time of the energy tool during the surgery); whereas "activation momentum" can be calculated in terms of the number of activations during each tool presence event (i.e., as the ratio of the activation-event count during a given on-screen presence period of the energy tool to the duration of the given on-screen presence time). In some embodiments, calculating the activation momentum requires the collaboration of the tool presence/absence detection model, which is used to determine the beginning (i.e., the moment when the tool enters the screen) and the end (i.e., the moment when the tool leaves the screen) of each detected tool presence event. Note that each detected tool presence event can correspond to a particular surgical task/step.

Figure 12:
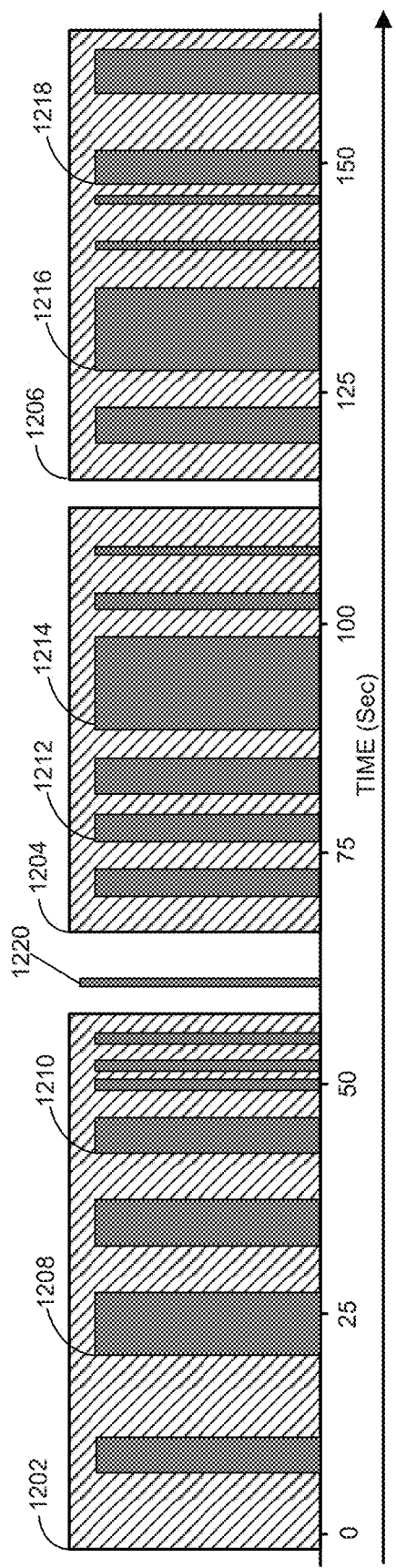
FIG. 12 presents a visual diagram that represents model inference outputs from both the disclosed activation detection model and the energy-tool presence/absence detection model applied on the same portion of a surgical video in accordance with some embodiments described herein.

FIG. 12 presents a visual diagram 1200 that represents model inference outputs from both the disclosed activation detection model and the energy-tool presence/absence detection model applied on the same portion of a surgical video in accordance with some embodiments described herein. As can be seen in FIG. 12, three exemplary inferred tool present events/durations from the tool presence/absence detection model are represented by a row of three rectangular boxes 1202, 1204, and 1206 filled with rectilinear patterns positioned on a time axis in the unit of seconds. The exemplary outputs from the disclosed activation detection model are represented by a row of dark grey bars of different widths (i.e., of different detected activation durations) and separated by different time intervals, and superimposed onto the inferred tool present events. As a result, it is straightforward to visualize which detected activations events are associated with a given inferred tool present event. For example, exemplary detected activation events 1208 and 1210 are associated with inferred tool present event 1202, exemplary detected activation events 1212 and 1214 are associated with inferred tool present event 1204, and exemplary detected activation events 1216 and 1218 are associated with inferred tool present event 1206. Note that there is also an exemplary detected activation event 1220 that does not belong to any of the inferred present event. It turns out that activation event 1220 is a false positive (FP) output from the activation detection model. As such, using visual diagram 1200 to visualize the inference outputs of the disclosed activation detection model and the tool presence/absence detection mode can provide various insights into the energy tool usage.

Activation Detection Model Use Case #3

The disclosed activation detection model and technique can be combined with the energy tool presence/absence detection model and technique disclosed to help detect and mitigate a type of energy tool off-screen risk in real-time. Note that the tool presence/absence detection model not only allows each on-screen presence of the energy tool to be detected, but also allows each off-screen duration between two consecutive on-screen presences of the energy tool to be detected. Specifically, the energy tool off-screen risk to be detected is when the energy tool is off-screen (i.e., not present in the endoscope view) and not activated, but the blades/jaws of the energy tool remain hot due to a most-recent activation. Note that when the hot jaws from the recent energy tool use are off-screen and therefore not visible to the user of the energy tool, injuries to the tissues become a potential risk from the hot tool. Clearly, to detect the hot jaws that are off-screen, it is necessary to detect both whether the tool is hot and whether the tool is off-screen, In some embodiments, to detect a hot energy tool, we can establish a mapping between the duration of an activation event and the resulting temperature of the one or both jaws after the activation. A high temperature threshold can also be set to define a condition referred to as "hot tool" that can cause injuries. During operation, the disclosed activation detection model can be applied to a real-time endoscope video to generate an activation duration prediction for each detected activation event. At the same time, the mapping profile between the activation duration and the resulting temperature can be used to predict the resulting temperature of the jaws from each newly-detected activation. Immediately after, the "hot tool" threshold can be compared with the predicted temperature, and trigger a "hot tool" detection if the threshold temperature is exceeded. Meanwhile, the tool presence/absence detection model can be independently and simultaneously applied the real-time endoscope video to detect when the jaws of the energy tool are off-screen. Hence, the combined detection results of the two detection models allow us to detect an "off-screen hot-tool" event, i.e., the tool off-screen risk in real time. Note that in this use case, there is no need for the logs from the energy tool generator, such as Ethicon™ Gen1™.

Figures 13A, 13B:
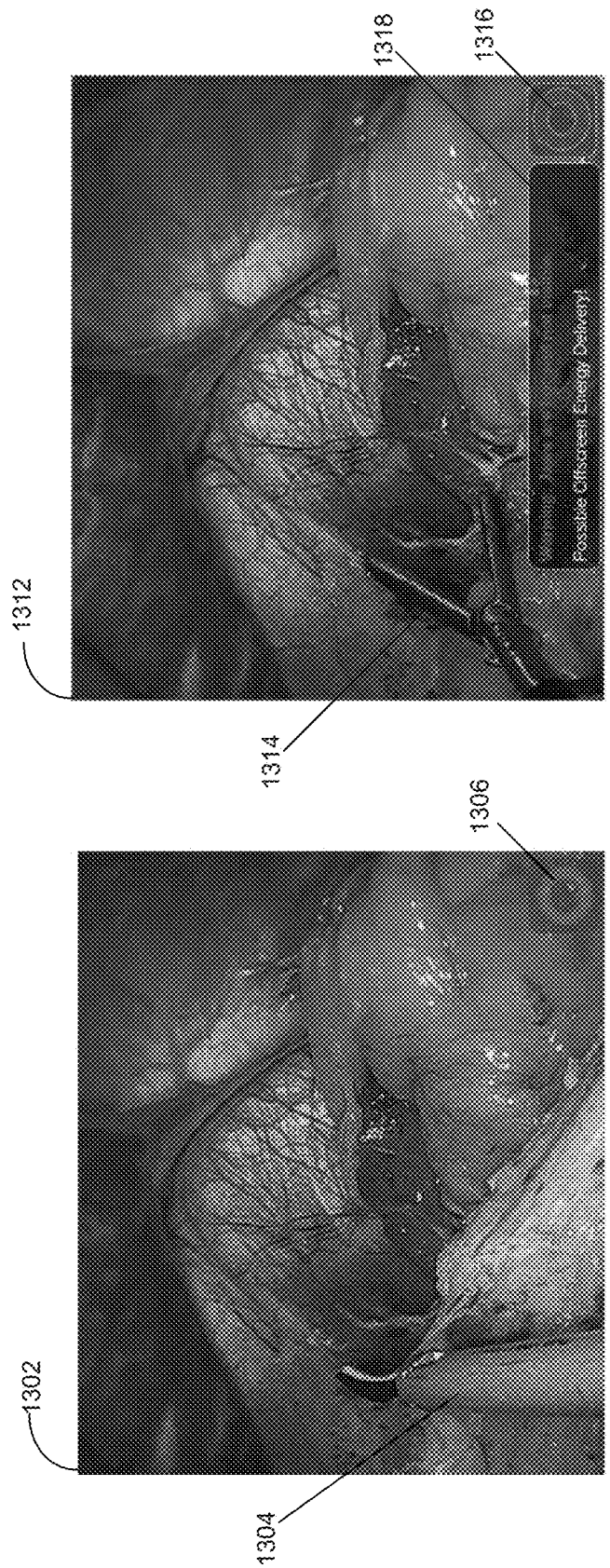
FIG. 13A shows an endoscope video frame illustrating an exemplary "safe use" scenario when the energy tool is present on screen in accordance with some embodiments described herein.
FIG. 13B shows an endoscope video frame illustrating an exemplary "unsafe use" scenario when the energy tool is off-screen but not activated in accordance with some embodiments described herein.

FIG. 13A shows an endoscope video frame 1302 illustrating an exemplary "safe use" scenario when an energy tool 1304 is present on screen in accordance with some embodiments described herein. Note that in video frame 1302, the "hot tool" detection technique based on the disclosed activation detection model does not detect a "hot tool" condition, which is indicated by a green circle 1306 at the lower right corner of video frame 1302.

In contrast, FIG. 13B shows an endoscope video frame 1312 illustrating an exemplary "unsafe use" scenario when the energy tool is off-screen but not activated in accordance with some embodiments described herein. Note that in video frame 1312, a different tool (i.e., a pair of forceps 1314) is visible but the energy tool 1304 is not visible (i.e., off-screen). Moreover, the "hot tool" detection technique based on the activation detection model has detected a "hot tool" condition associated with the off-screen energy tool 1304, which is indicated by a red circle 1316 at the lower right corner of video frame 1312. As a result, an "off-screen hot-tool" event is detected, which can immediately trigger a warning message 1318 to be displayed on the screen, as shown in video frame 1312. Note that the above disclosed off-screen/hot-tool risk detection technique can mitigate the risk of potential injuries from the hot jaws of energy tools to significantly increase usage safety of the energy tools, without relying on any internal logging functionality. Hence, the disclosed off-screen/hot-tool risk detection function can be implemented on any energy tool as an extra safety feature.

Activation Detection Model Use Case #4

Note that the outputs from the disclosed activation detection model applied on a surgical video can be used to develop additional statistical metrics for assessing the quality of energy tool usage, such as the activation efficiency during the surgical procedure. For example, the statistical metrics that can be computed based on the activation detection outputs can include, but are not limited to: the total activation time/duration; and the total number of activations. In some embodiments, the tool present/absent detection model can be applied to the same surgical video to generate another useful statistical metric: the total presence time/duration of the energy tool. These activation and presence statistical metrics can be computed for a set of videos from a batch of surgical cases involving energy tools. Next, the computed statistical metrics for the batch of surgical cases can be combined with other general surgical case data, such as, case #s, hospitals, procedure types, energy devices types, to generate a combined report on the batch of surgical cases, which can be presented to surgeons in the form of a table, referred to as an "energy dosage" table.

FIG. 17 shows Table 2 which is an exemplary energy dosage table compiled for 20 sleeve gastrectomy cases including both tool activation and tool presence statistical metrics in accordance with some embodiments described herein. Note that by using the energy dosage table, activation and presence statistical metrics, including total presence duration C7, total activation duration C8, and total number of activations C9 can be easily compared among the batch of 20 cases combined in Table 2. Note that the data shown in the energy dosage table can also be shown by graphs. By computing, compiling, and comparing these tool activation and presence statistical metrics, a number of surgical insights can be drawn from the data for each case. For example, by observing at how frequently the energy tool was fired during its presence, i.e., the ratio of number of activations in C9 to the total presence duration in C7, it is possible to gain insights in the effectiveness of the energy tool use, the skill level of the surgeon, and the difficulty level of the case. While only the full procedure activation and presence statistical metrics are shown in the energy dosage table, these statistical metrics can also be extracted for particular surgical steps and surgical tasks that involve the energy tool use to gain insights on how the energy tool was used during each particular surgical step and/or task.

Note that developing statistical metrics based on the activation detection model outputs should be considered an offline usage/functionality of the model that primarily used to generate retrospective statistical insights about surgical procedures, and/or to display such information on an online surgical video review platform, such as the C-SATS™ portal. Using this offline functionality, a surgeon can be informed of how an energy tool was used during a full surgical procedure, and during particular surgical steps and/or tasks. This functionality can also help to uncover alternative techniques that a surgeon can employ to improve his/her energy tool usage efficiency and/or quality of skill. Using the compiled statistical metrics in table or graph forms, the surgeons will also be able to compare these statistics among their own cases performed at different times, or to compare their statistics with other cases performed by other surgeons, thereby allowing them to improve the performance of their surgical care. In addition to the training aspect of this use case, the post-analysis natures of this usage can also lead to other innovative product solutions.

Activation Detection Model Use Case #5

In addition to generating the generic "surgical momentum" metric, which is a scalar number that quantifies the activation rate for the entire surgery, the video processing output of the disclosed activation detection model can also be used to calculate a dynamic activation rate that monitors in real-time how many activations take place within a shorter time window. For example, an activation rate/momentum can be calculated at every 60 seconds during the surgery or at some other short time windows. We refer to this activation rate/momentum continuously computed over a short time window as a "continuous momentum" metric. Note that this continuous momentum metric can be used to monitor "deceleration" and "acceleration" of the activation rate, i.e., whether the activation rate/momentum is decreasing or increasing in the last short time window, e.g., the last 60 seconds. Note that this continuous momentum metric can be used to gain and discover a number of clinical-insights. Some of these clinical-insights related to the continuous momentum metric are as follows:

Anatomical complexities and variations including obesity, prominent or aberrant vasculature, and adhesions can make surgical tool navigation around the surgical sites more difficult, leading to a slower rate of activations and hence a lower value of the continuous momentum;

The continuous momentum metric can be used as an indicator of the level of expertise and experience of a given surgeon, because new or inexperienced surgeons tend to conduct the surgical tasks, including those tasks that involve the energy tools at a slower pace;

The continuous momentum metric can be used to evaluate and compare the proficiencies of different perioperative teams and surgical assistants, because a more proficient or attuned assistant can facilitate a faster rate of activations by the primary operating surgeon; and Intraoperative surgical judgment by a surgeon can also have an effect on the continuous momentum. A higher rate of task switching by the surgeon may decrease the continuous momentum. Hence, the continuous momentum metric can be an indicator of how efficiently and rapidly a surgeon switches surgical tasks and manages the surgical workflow.

Surgical Video Processing Pipeline for Post-Surgery Data Analysis

Figure 14:
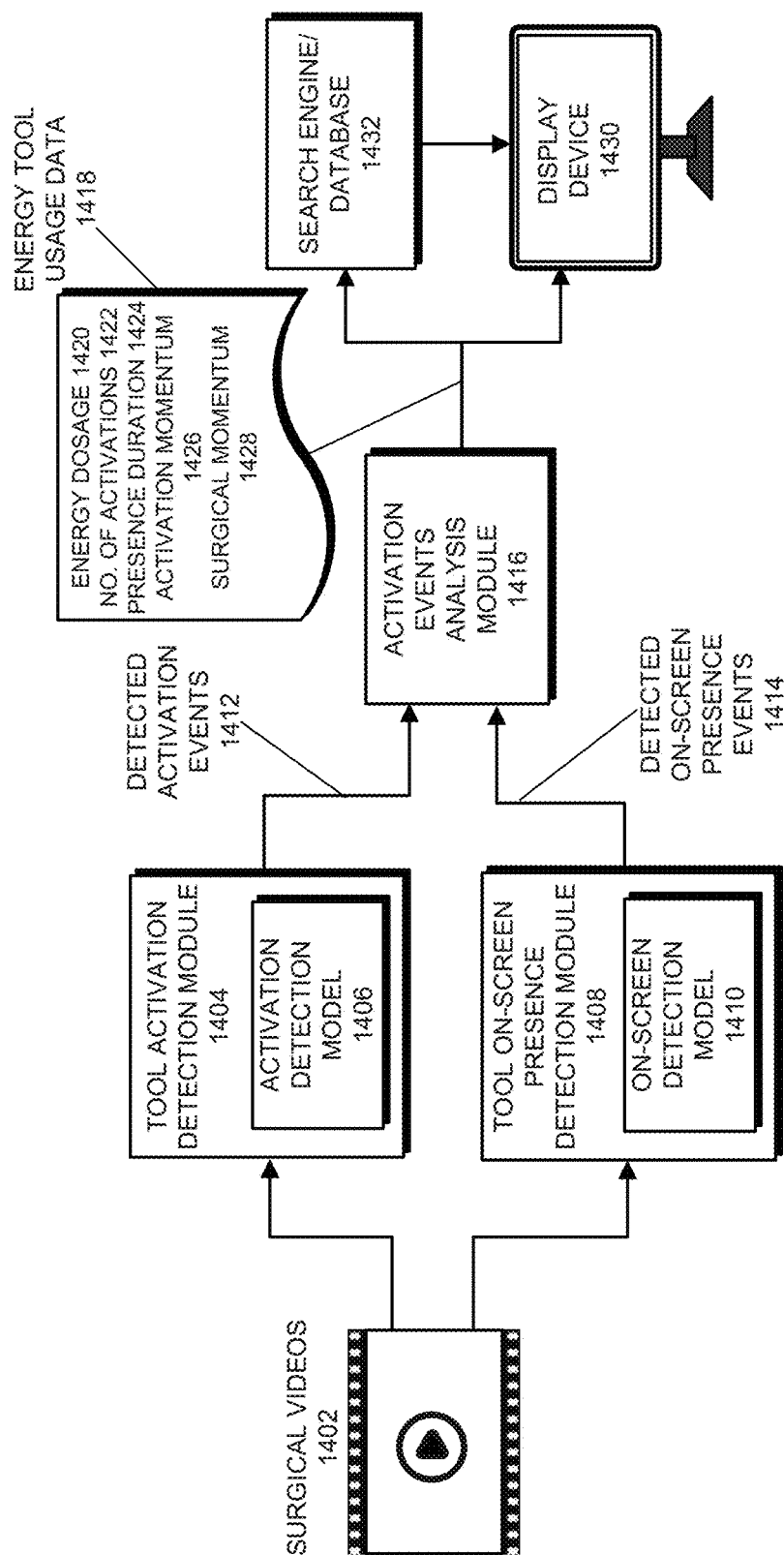
FIG. 14 show a block diagram of a surgical video processing and analysis system that leverages the disclosed activation detection model and the energy-tool presence/absence detection model to generate a variety of tool usage statistical metrics for post-surgery analyses and search-engine applications in accordance with some embodiments described herein.

FIG. 14 show a block diagram illustrating a surgical video processing and analysis system 1400 that leverages the disclosed activation detection model and the energy-tool presence/absence detection model to generate a variety of tool usage statistical metrics for post-surgery data analyses and search-engine applications in accordance with some embodiments described herein. As can be seen in FIG. 14, surgical video processing and analysis system 1400 (or "processing and analysis system 1400") receives a collection of surgical videos 1402 of a surgical procedure involving an energy tool, e.g., a gastric bypass procedure or a sleeve gastrectomy procedure. In some embodiments, the collection of surgical videos 1402 is associated with a collection of surgical cases performed by a diverse group of surgeons. In some embodiments, the collection of surgical videos 1402 is associated with a collection of surgical cases performed using a variety of energy tool types and models including, but not limited to Harmonic™, LigaSure™, Enseal™, Sonicision™.

Processing and analysis system 1400 can include two video processing paths: the first path that includes a tool activation detection module 1404 and the second path that includes a tool on-screen presence detection module 1408. Tool activation detection module 1404 uses the disclosed activation detection module 1406 to perform the disclosed energy tool activation/non-activation inferences on each received surgical video 1402 and subsequently outputs a sequence of detected activation events 1412 for the surgical video. In some embodiments, each detected activation event in the sequence of detected activation events 1412 includes an identified starting timestamp and a duration of the detected activation event. Concurrently or in parallel, tool on-screen presence detection module 1408 uses an energy-tool presence/absence detection model 1410 to perform energy tool presence/absence inferences on each received surgical video 1402 and subsequently outputs a sequence of detected on-screen presence events 1414 corresponding to a sequence of surgical tasks of the surgical procedure. In some embodiments, each detected on-screen presence event includes an identified starting timestamp of the detected on-screen presence event and a duration of the detected on-screen presence event.

Processing and analysis system 1400 also includes an activation events analysis module 1416 which receives both the sequence of detected activation events 1412 and the sequence of detected on-screen presence events 1414 as inputs, and extracts/generates a set of energy tool usage data 1418 based on the detected activation events 1412 and the detected on-screen presence events 1414 as outputs. In some embodiments, extracting the set of energy tool usage data 1418 involves: (1) superimposing (temporally) the detected sequence of activation events and the detected set of on-screen presence events to identify within the duration of each detected on-screen presence event, a subset of the detected activation events associated with a corresponding surgical task; and then (2) extracting a set of energy tool usage data associated with the corresponding surgical task based on the identified subset of the detected activation events. An example process of superimposing the two sequences of detected events is shown in FIG. 12.

As can be seen in FIG. 14, the set of energy tool usage data 1418 generated by activation events analysis module 1416 can include: (1) the energy dosage 1420 for each surgical task; (2) the number of activation events 1422 for each surgical task; (3) the tool on-screen presence duration 1424 for each surgical task; (4) an activation momentum metric 1426 for each surgical task; and (5) a surgical momentum metric 1428 for the surgical procedure. In some embodiments, the energy dosage 1420 delivered during a given surgical task is determined based on the total activation duration of the identified subset of the detected activation events associated with the given surgical task. In some embodiments, the activation momentum metric 1426 is computed as the ratio of the total number of detected activation events within the duration of the detected on-screen presence event to the duration of the detected on-screen presence event. In some embodiments, to compute the surgical momentum metric 1428, we (1) compute a combined duration of the sequence of detected on-screen presence events for the surgical video; and (2) count a total number of the detected activation events in the surgical video. We then compute the surgical momentum metric as the ratio of the total number of detected activation events in the surgical video to the combined duration of the sequence of detected on-screen presence events.

In some embodiments, the set of energy tool usage data 1418 can also include a nominal number of activations of each surgical task for the plurality of surgical videos 1402 obtained by averaging the set of determined numbers of activation events of the surgical task for the plurality of surgical videos 1402. In some embodiments, the set of energy tool usage data 1418 additionally includes a nominal energy dosage used in each surgical task for the plurality of surgical videos 1402 obtained by averaging the set of determined energy dosages for the surgical task for the plurality of surgical videos 1402.

Note that surgical video processing and analysis system 1400 can include or alternatively be coupled to a display device 1430 for visually present some or all of the extracted energy tool usage data 1418 from individual surgical video 1402 or the match of surgical videos 1402 to a user. Surgical video processing and analysis system 1400 is also configured to visually present the detection outputs from activation detection module 1404 and on-screen presence detection module 1408 on display device 1430. For example, surgical video processing and analysis system 1400 can generate and display on display device 1430 the visual diagram 1200 shown in FIG. 12 based on the sequence of detected activation events 1412 and the sequence of detected on-screen presence events 1414.

Surgical video processing and analysis system 1400 can also include or alternatively be coupled to a search engine/database 1432. Specifically, the extracted energy tool usage data 1418, the detected activation events 1412, and the detected on-screen presence events 1414 can be stored within search engine/database 1432 and indexed based on the corresponding set of energy tool usage metrics. In some embodiments, storing the extracted energy tool usage data 1418 in search engine/database 1432 includes separating the extracted set of energy tool usage data 1418 into a set of categories corresponding to the set of energy tool usage metrics, and further separating the extracted energy tool usage data within each category of the set of categories into a set of subcategories of the corresponding energy tool usage metric.

For example, the set of main categories that is used to index the energy tool usage data 1418 can include: (1) the energy dosage; (2) the number of activations; (3) the energy tool on-screen presence duration; and (4) the number of activations per unit time. In some embodiments, the set of subcategories under the energy dosage category can include: (1) Low; (2) Normal; and (3) High. In some embodiments, the set of subcategories under the number of activations category can include: (1) Frequent; (2) Average; and (3) Infrequent. In some embodiments, the set of subcategories under the on-screen presence duration category can include: (1) Low; (2) Normal; and (3) High. In some embodiments, the set of subcategories under to the on-screen presence duration category can include: (1) Short; (2) Normal; and (3) Long. In some embodiments, the set of subcategories under the number of activations per unit time category can include: (1) Low; (2) Normal; and (3) High. The above are just some examples of the categories and corresponding subcategories for indexing the energy tool usage data 1418 in search engine/database 1432. In some embodiments, search engine/database 1432 is configured with a query function. Hence, when a search request/query from a user on a given energy tool usage metric is received by search engine/database 1432, search engine/database 1432 can search in and return from the database portion of the search engine/database 1432, the stored energy tool usage data that match the requested usage metric. In some embodiments, the returned energy tool usage data can be visually and/or graphically presented to the user on display device 1430. In some embodiments, search engine/database 1432 can be implemented as two separate modules: a search engine module for performing the above-described search/query functions; and a database module for performing the above-described indexed storage functions. In some embodiments, the database portion of search engine/database 1432 can be located on a database server or in the Cloud.

Figure 15:
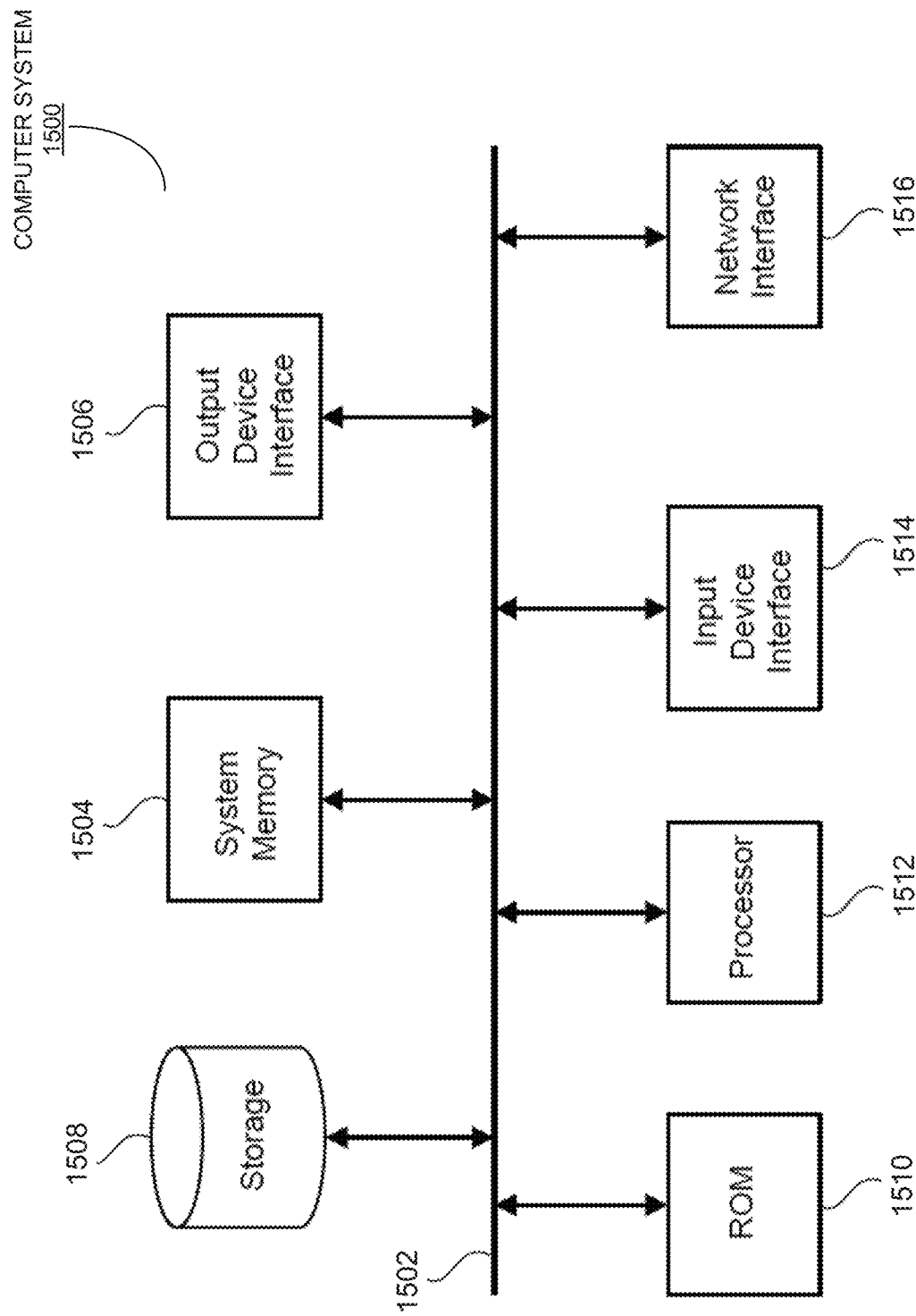
FIG. 15 conceptually illustrates a computer system with which some embodiments of the subject technology can be implemented.

FIG. 15 conceptually illustrates a computer system with which some embodiments of the subject technology can be implemented. Computer system 1500 can be a client, a server, a computer, a smartphone, a PDA, a laptop, or a tablet computer with one or more processors embedded therein or coupled thereto, or any other sort of computing device. Such a computer system includes various types of computer-readable media and interfaces for various other types of computer-readable media. Computer system 1500 includes a bus 1502, processing unit(s) 1512, a system memory 1504, a read-only memory (ROM) 1510, a permanent storage device 1508, an input device interface 1514, an output device interface 1506, and a network interface 1516. In some embodiments, computer system 1500 is a part of a robotic surgical system.

Bus 1502 collectively represents all system, peripheral, and chipset buses that communicatively connect the numerous internal devices of computer system 1500. For instance, bus 1502 communicatively connects processing unit(s) 1512 with ROM 1510, system memory 1504, and permanent storage device 1508.

From these various memory units, processing unit(s) 1512 retrieves instructions to execute and data to process in order to execute various processes described in this patent disclosure, including the above-described processes for annotating raw surgical videos in preparation for constructing a training dataset described in conjunction with FIGS. 1-3, the above-described processes for constructing the training dataset for training/validation the disclosed activation detection models described in conjunction with FIGS. 4-8, and the above-described processes for using the disclosed activation detection model to detect energy tool activation events in a surgical video, and output tool activation measurements (i.e., activation durations and counts) described in conjunction with FIG. 9. The processing unit(s) 1512 can include any type of processor, including, but not limited to, a microprocessor, a graphic processing unit (GPU), a tensor processing unit (TPU), an intelligent processor unit (IPU), a digital signal processor (DSP), a field-programmable gate array (FPGA), and an application-specific integrated circuit (ASIC). Processing unit(s) 1512 can be a single processor or a multi-core processor in different implementations.

ROM 1510 stores static data and instructions that are needed by processing unit(s) 1512 and other modules of the computer system. Permanent storage device 1508, on the other hand, is a read-and-write memory device. This device is a non-volatile memory unit that stores instructions and data even when computer system 1500 is off. Some implementations of the subject disclosure use a mass-storage device (such as a magnetic or optical disk and its corresponding disk drive) as permanent storage device 1508.

Other implementations use a removable storage device (such as a floppy disk, flash drive, and its corresponding disk drive) as permanent storage device 1508. Like permanent storage device 1508, system memory 1504 is a read-and-write memory device. However, unlike storage device 1508, system memory 1504 is a volatile read-and-write memory, such as a random access memory. System memory 1504 stores some of the instructions and data that the processor needs at runtime. In some implementations, various processes described in this patent disclosure, including the above-described processes and techniques for annotating raw surgical videos in preparation for constructing a training dataset described in conjunction with FIGS. 1-3, the above-described processes and techniques for constructing the training dataset for training/validation the disclosed activation detection models described in conjunction with FIGS. 4-8, and the above-described processes and techniques for using the disclosed activation detection model to detect energy tool activation events in a surgical video, and output tool activation measurements (i.e., activation durations and counts) described in conjunction with FIG. 9, are stored in system memory 1504, permanent storage device 1508, and/or ROM 1510. From these various memory units, processing unit(s) 1512 retrieves instructions to execute and data to process in order to execute the processes of some implementations.

Bus 1502 also connects to input and output device interfaces 1514 and 1506. Input device interface 1514 enables the user to communicate information to and select commands for the computer system. Input devices used with input device interface 1514 include, for example, alphanumeric keyboards and pointing devices (also called "cursor control devices"). Output device interface 1506 enables, for example, the display of images generated by the computer system 1500. Output devices used with output device interface 1506 include, for example, printers and display devices, such as cathode ray tubes (CRT) or liquid crystal displays (LCD). Some implementations include devices such as a touchscreen that functions as both input and output devices.

Finally, as shown in FIG. 15, bus 1502 also couples computer system 1500 to a network (not shown) through a network interface 1516. In this manner, the computer can be a part of a network of computers (such as a local area network ("LAN"), a wide area network ("WAN"), an intranet, or a network of networks, such as the Internet. Any or all components of computer system 1500 can be used in conjunction with the subject disclosure.

The various illustrative logical blocks, modules, circuits, and algorithm steps described in connection with the embodiments disclosed in this patent disclosure may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The hardware used to implement the various illustrative logics, logical blocks, modules, and circuits described in connection with the aspects disclosed herein may be implemented or performed with a general purpose processor, a digital signal processor (DSP), an application-specific integrated circuit (ASIC), a field-programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of receiver devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored as one or more instructions or code on a non-transitory computer-readable storage medium or non-transitory processor-readable storage medium. The steps of a method or algorithm disclosed herein may be embodied in processor-executable instructions that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable storage media may include RAM, ROM, EEPROM, flash memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable storage medium and/or computer-readable storage medium, which may be incorporated into a computer-program product.

While this patent document contains many specifics, these should not be construed as limitations on the scope of any disclosed technology or of what may be claimed, but rather as descriptions of features that may be specific to particular embodiments of particular techniques. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described, and other implementations, enhancements and variations can be made based on what is described and illustrated in this patent document.

What is claimed is:

1. A computer-implemented method, comprising:
receiving a surgical video of a surgical procedure involving energy tool activations;
applying a sequence of sampling windows to the surgical video to generate a sequence of windowed samples of the surgical video;
for each windowed sample in the sequence of windowed samples, applying a deep-learning model to a sequence of video frames within the windowed sample to generate an activation/non-activation inference and a confidence level associated with the activation/non-activation inference, thereby generating a sequence of activation/non-activation inferences and a sequence of associated confidence levels; and
identifying a sequence of activation events based on the sequence of activation/non-activation inferences and the sequence of associated confidence levels, wherein identifying an activation event in the sequence of activation events comprises:
identifying multiple consecutive activation inferences located between two non-activation inferences, in the sequence of activation/non-activation inferences, as a single activation;
identifying the first and the last inferences in the multiple consecutive activation inferences corresponding to two partial-activation windowed samples that partially overlap with the activation event;
determining first and second amounts of partial-overlap between the two partial-activation windowed samples, respectively, and the activation event, based on the confidence levels associated with the first and the last inferences; and
computing a duration of the activation event, wherein the duration comprises a sum of the first and second amounts of partial-overlap.

2. The computer-implemented method of claim 1, wherein the method further comprises generating a total activation count for the surgical video by:
incrementing an activation count by one in response to the multiple consecutive activation inferences; and
outputting a final-updated activation count as the total activation count for the surgical video after processing the sequence of activation/non-activation inferences.

3. The computer-implemented method of claim 1, wherein determining the first and second amounts of partial-overlap includes multiplying a window length of the windowed sample with the confidence level associated with the first or the last inference.

4. The computer-implemented method of claim 1, wherein the sequence of sampling windows has a common window length determined based on an activation duration distribution of a large number of previously-identified activation events from a plurality of surgical videos of the surgical procedure.

5. The computer-implemented method of claim 1, wherein applying the sequence of sampling windows includes adding a predetermined amount of overlap between consecutive sampling windows.

6. The computer-implemented method of claim 1, wherein the method further comprises training the deep-learning model by:
receiving a group of annotated surgical videos of the surgical procedure, wherein each annotated surgical video in the group of annotated surgical videos includes a set of identified activation events, wherein each identified activation event is annotated with a starting timestamp and an end timestamp;
for each annotated surgical video in the group of annotated surgical videos, generating a set of labeled training data by sampling the annotated surgical video;
adding the set of labeled training data into a training dataset; and
training the deep-learning model using the training dataset.

7. The computer-implemented method of claim 6, wherein generating the set of labeled training data by sampling the annotated surgical video includes:
sequentially applying a sequence of sampling windows to the annotated surgical video to generate a sequence of windowed samples of the annotated surgical video; and
for each windowed sample in the sequence of windowed samples,
acquiring a ground truth label for the windowed sample based on the temporal location of the windowed sample with respect to the set of annotated activation events in the annotated surgical video; and
adding the labeled windowed sample into the set of labeled training data.

8. The computer-implemented method of claim 7, wherein acquiring the ground truth label for the windowed sample based on the temporal location of the windowed sample includes:
providing a first integer label of "1" to the windowed sample if the windowed sample is situated entirely inside an annotation activation event within the set of annotated activation events; and
providing a second integer label of "0" to the windowed sample if the windowed sample is situated entirely outside of any of the set of annotated activation events.

9. The computer-implemented method of claim 8, wherein acquiring the ground truth label for the windowed sample further comprises:
providing a float number label between "0" and "1" to the windowed sample if the windowed sample partially overlaps with an annotated activation event within the set annotated activation events, wherein the float number label is computed based on the percentage of the windowed sample positioned inside the identified activation event.

10. The computer-implemented method of claim 9, wherein the method further comprises:
providing a negative sign to the float number label assigned to the windowed sample if the windowed sample overlaps with the beginning portion of the annotated activation event; and
providing a positive sign to the float number label assigned to the windowed sample if the windowed sample overlaps with the ending portion of the annotated activation event.

11. The computer-implemented method of claim 9, wherein the method further comprises:
determining whether the center video frame within the windowed sample is inside the annotated activation event; and
in response to determining that the center video frame is outside of the annotated activation event, excluding the windowed sample from the training dataset.

12. A system for automatically detecting energy tool activations, the system comprising:
one or more processors; and
a memory coupled to the one or more processors; and
wherein the memory stores a set of instructions that, when executed by the one or more processors, cause the system to:
receive a surgical video of a surgical procedure involving energy tool activations;
apply a sequence of sampling windows to the surgical video to generate a sequence of windowed samples of the surgical video;
for each windowed sample in the sequence of windowed samples, apply a deep-learning model to a sequence of video frames within the windowed sample to generate an activation/non-activation inference and a confidence level associated with the activation/non-activation inference, thereby generating a sequence of activation/non-activation inferences and a sequence of associated confidence levels; and
identify a sequence of activation events based on the sequence of activation/non-activation inferences and the sequence of associated confidence levels, wherein identifying an activation event in the sequence of activation events comprises:
identifying multiple consecutive activation inferences located between two non-activation inferences, in the sequence of activation/non-activation inferences, as a single activation;
identifying the first and the last inferences in the multiple consecutive activation inferences corresponding to two partial-activation windowed samples that partially overlap with the activation event;
determining first and second amounts of partial-overlap between the two partial-activation windowed samples, respectively, and the activation event, based on the confidence levels associated with the first and the last inferences; and
computing a duration of the activation event, wherein the duration comprises a sum of the first and second amounts of partial-overlap.

13. The system of claim 12, wherein the memory stores a set of instructions that, when executed by the one or more processors, cause the system to generate a total activation count for the surgical video by:
incrementing an activation count by one in response to the detection of the one or more consecutive activation inferences; and
outputting a final-updated activation count as the total activation count for the surgical video after processing the sequence of activation/non-activation inferences.

14. A computer-implemented method of constructing a training dataset for training an energy tool activation detection model, the method comprising:
receiving multiple sequences of annotated activation events from a group of annotators independently annotating a surgical video, wherein each sequence of annotated activation events is extracted from each independently annotated surgical video;
performing a temporal clustering on the multiple sequences of annotated activation events to group annotated activation events in the multiple sequences of annotated activation events into clusters of annotated activation events, wherein each cluster of annotated activation events belongs to the same activation event in the surgical video;
computing statistical consensuses for each cluster of the annotated activation events;
comparing each annotated activation event within the cluster of annotated activation events with the computed statistical consensuses of the cluster of annotated activation events to identify an anomaly within the cluster of annotated activation events;
in response to identifying an anomaly associated with an annotated activation event in the cluster of annotated activation events, updating the cluster of annotated activation events by replacing the associated annotated activation event with updated annotations of the associated activation event to eliminate the anomaly; and
outputting the computed statistical consensuses as ground truth for the associated activation event in a subsequent model building process.

15. The computer-implemented method of claim 14, wherein each sequence of annotated activation events in the multiple sequences of annotated activation events includes a first annotated activation event positioned between two non-activation periods, and wherein the first annotated activation event includes an annotated starting timestamp and an annotated end timestamp.

16. The computer-implemented method of claim 15, wherein computing the statistical consensuses for each cluster of the annotated activations includes computing a first mean value of a set of annotated starting timestamps within the cluster of annotated activation events, and a second mean value of a set of annotated end timestamps within the cluster of annotated activation events.

17. The computer-implemented method of claim 14, wherein after updating the cluster of annotated activation events, the method further comprises:
recomputing statistical consensuses for the cluster of the annotated activation events; and outputting the recomputed statistical consensuses as ground truth for the associated activation event in the subsequent model building process.

* * * * *